US008178562B2

(12) United States Patent
Bolli et al.

(10) Patent No.: US 8,178,562 B2
(45) Date of Patent: May 15, 2012

(54) PYRIDINE DERIVATIVES

(75) Inventors: Martin Bolli, Allschwil (CH); David Lehmann, Basel (CH); Boris Mathys, Pratteln (CH); Claus Mueller, Weil Am Rhein (DE); Oliver Nayler, Arlesheim (CH); Beat Steiner, Battwil (CH); Joerg Velker, Huningue (FR)

(73) Assignee: Actelion Pharmaceuticals, Ltd., Allschwil (CH)

( * ) Notice: Subject to any disclaimer, the term of this patent is extended or adjusted under 35 U.S.C. 154(b) by 763 days.

(21) Appl. No.: 12/161,909

(22) PCT Filed: Jan. 23, 2007

(86) PCT No.: PCT/IB2007/050225
§ 371 (c)(1),
(2), (4) Date: Jul. 23, 2008

(87) PCT Pub. No.: WO2007/086001
PCT Pub. Date: Aug. 2, 2007

(65) Prior Publication Data
US 2009/0005421 A1 Jan. 1, 2009

(30) Foreign Application Priority Data

Jan. 24, 2006 (WO) .................. PCT/IB2006/050260

(51) Int. Cl.
*A61K 31/443* (2006.01)
*C07D 413/14* (2006.01)
(52) U.S. Cl. .................................. 514/340; 546/269.4
(58) Field of Classification Search ................ 546/269.4; 514/340
See application file for complete search history.

(56) References Cited

U.S. PATENT DOCUMENTS

| 4,808,599 | A | 2/1989 | Dubroeucq et al. |
| 6,156,787 | A | 12/2000 | Broughton et al. |
| 7,723,378 | B2 | 5/2010 | Bolli et al. |
| 8,003,800 | B2 | 8/2011 | Bolli et al. |
| 2004/0058894 | A1 | 3/2004 | Doherty et al. |
| 2006/0293252 | A1 | 12/2006 | Glombik et al. |
| 2008/0005421 | A1 | 1/2008 | Chang et al. |
| 2008/0064740 | A1 | 3/2008 | Bolli et al. |
| 2008/0176926 | A1 | 7/2008 | Bolli et al. |
| 2008/0194670 | A1 | 8/2008 | Bolli et al. |
| 2008/0300294 | A1 | 12/2008 | Bolli et al. |
| 2008/0318955 | A1 | 12/2008 | Bolli et al. |
| 2010/0075946 | A1 | 3/2010 | Bolli et al. |
| 2010/0204198 | A1 | 8/2010 | Bolli et al. |

FOREIGN PATENT DOCUMENTS

| EP | 0 310 321 | | 4/1989 |
| EP | 0 476 646 | A1 | 3/1992 |
| GB | 2 336 588 | | 10/1999 |
| WO | WO-91/15583 | A1 | 10/1991 |
| WO | WO-99/46277 | A1 | 9/1999 |
| WO | WO-03/014107 | A1 | 2/2003 |
| WO | WO 03/062248 | | 7/2003 |
| WO | WO 03/062252 | | 7/2003 |
| WO | WO 03/105771 | | 12/2003 |
| WO | WO 2004/007517 | | 1/2004 |
| WO | WO-2004/010949 | A2 | 2/2004 |
| WO | WO-2004/035538 | A1 | 4/2004 |
| WO | WO 2004/103279 | | 12/2004 |
| WO | WO-2005/014525 | A2 | 2/2005 |
| WO | WO-2005/032465 | A2 | 4/2005 |
| WO | WO-2005/058848 | A1 | 6/2005 |
| WO | WO 2006/010379 | | 2/2006 |
| WO | WO 2006/010544 | | 2/2006 |
| WO | WO 2006/100631 | | 9/2006 |
| WO | WO 2006/131336 | | 12/2006 |
| WO | WO-2006/131336 | A1 | 12/2006 |
| WO | WO 2007/085451 | | 8/2007 |
| WO | WO-2007/085451 | A2 | 8/2007 |
| WO | WO-2008/076356 | A1 | 6/2008 |

OTHER PUBLICATIONS

Hla et al., The Journal of Biological Chemistry, vol. 265, pp. 9308-9313 (1990).
Philip L. Gould, International Journal of Pharmaceutics, vol. 33, pp. 201-217 (1986).
Table of Content of "Pharmaceutical Preformulation and Formulation", A Practical Guide from Candidate Drug Selection to Commerical Dosage Form, edited by Mark Gibson, IHS Health Group, Englewood, Colorado, U.S.A. (2001).
Table of Content of Greene et al., "Protective Groups in Organic Synthesis", Third Edition, Wiley New York (1991).
Table of Content of P.J. Kocienski, "Protecting Groups", Thieme Stuttgart (1994).
Brain et al., Tetrahedron Letters, vol. 40, pp. 3275-3278 (1999).
Bentiss et al., Synthetic Communications, vol. 31, pp. 935-938 (2001).
Tandon et al., Synthetic Communications, vol. 31, pp. 1727-1732 (2001).
Hamze et al., J. Org. Chem., vol. 68, pp. 7316-7321 (2003).
Gangloff et al., Tetrahedron Letters, vol. 42, pp. 1441-1443 (2001).
Suzuki et al., Chem. Pharm. Bull., vol. 47, pp. 120-122 (1999).
Poulain et al., Tetrahedron Letters, vol. 42, pp. 1495-1498 (2001).
Srivastava et al., Synthetic Communications, vol. 29, pp. 1437-1450 (1999).
John et al., Inorg. Chem., vol. 27, pp. 3100-3104 (1988).
Kaboudin et al., Heterocycles, vol. 60, pp. 2287-2292 (2003).
Cui et al., Bioorganic & Medicinal Chemistry, vol. 11, pp. 3379-3392 (2003).
Ren et al., J. Heterocyclic Chem., vol. 23, pp. 1757-1763 (1986).
Richard E. Mewshaw, Tetrahedron Letters, vol. 30, pp. 3753-3756 (1989).
Kashima et al., J. Heterocyclic Chem., vol. 40, pp. 773-782 (2003).
Yavari et al., Tetrahedron, vol. 59, pp. 2001-2005 (2003).
Konopelski et al., Organic Letters, vol. 4, pp. 4121-4124 (2002).
Wiles et al., Tetrahedron Letters, vol. 43, pp. 2945-2948 (2002).
Faure et al., Heterocycles, vol. 57, pp. 307-316 (2002).

(Continued)

*Primary Examiner* — Patricia Morris
(74) *Attorney, Agent, or Firm* — Hoxie & Associates LLC

(57) ABSTRACT

The invention relates to novel pyridine derivatives, their preparation and their use as pharmaceutically active compounds. Said compounds particularly act as immunosuppressive agents.

9 Claims, No Drawings

OTHER PUBLICATIONS

Hammadi et al., Synthetic Communications, vol. 26, pp. 2901-2904 (1996).
Flaugh et al., J. Org. Chem., vol. 45, pp. 5399-5400 (1980).
Natale et al., Organic Preparations and Procedures Int., vol. 9, pp. 103-108 (1977).
Rice et al., Journal of Heterocyclic Chemistry, vol. 10, pp. 731-735 (1973).
Cocker et al., Tetrahedron Letters, No. 51, pp. 4451-4452 (1969).
Lochynski et al., Journal f. prakt. Chemie, vol. 330, pp. 284-288 (1988).
Walkowicz et al., Roczniki Chemii Ann. Soc. Chim. Polonorum, vol. 41, pp. 927-937 (1967).
Pol et al., Indian J. Chem., vol. 19B, pp. 603-604 (1980).
Popov et al., Tetrahedron: Asymmetry, vol. 5, pp. 479-489 (1994).
Popov et al., Synthetic Communications, vol. 31, pp. 233-243 (2001).
Liu et al., J. Org. Chem., vol. 67, pp. 9267-9275 (2002).
Knight et al., Tetrahedron Letters, vol. 21, pp. 5051-5054 (1980).
R. Raap, Canadian Journal of Chemistry, vol. 49, pp. 2155-2157 (1971).
Lakhvich et al., Organic Chemistry Journal, vol. 25, Part 12, pp. 2541-2549 (1989) (w/English translation of same).
Kuczynski et al., Roczniki Chemii, Ann. Soc. Chim. Polonorum, vol. 38, pp. 1625-1633 (1964) (w/English translation of same).
Brinkmann, V. et al.; "The Immune Modulator FTY720 Targets Sphingosine 1-Phosphate Receptors"; The Journal of Biological Chemistry, vol. 277, No. 24, Jun. 14, 2002, pp. 21453-21457.
Matloubian, M. et al.;"Lymphocyte egress from thymus and peripheral lymphoid organs is dependent on S1P receptor 1"; Nature, vol. 427, Jan. 22, 2004. pp. 355-360.
Christi, M. et al.; "Einige Valene von benzanellierten fuenfgliedrigen Heteroarenen—Synthesen und NMR-Spektren"; Annewandte Chemie. vol. 102. No. 6, 1990, pp. 704-706.
Actelion: "Company Presention"; Internet Article, Nov. 2005, pp. 23-25.
Berge, S. et al.; "Pharmaceutical Salts"; Journal of Pharmaceutical Sciences, vol. 66, No. 1, Jan. 1977, pp. 1-19.
Mentzel, M. et al.; "N-Methoxy-N-methylamides (Weinreb Amides) in Modern Organic Synthesis"; Journal fuer praktische Chemie Chemiker-Zeitung, 339, (1997), pp. 517-524.
Singh, J. et al.; "The Growing Synthetic Utility of Weinreb's Amide"; Journal fuer Praktische Chemie (Weinheim, Germany), 342, (2000), pp. 340-347.
Khlestkin, V. et al.; "Recent Advances in the Application of N,O-Dialkylhydroxylamines in Organic Chemistry"; Current Organic Chemistry, 7, (2003), pp. 967-993.
Kuczynski, H. et al; "0 Krystalicznym (-)-Dwubromo-3,4-Karanie" Roczniki Chemii Ann. Soc. Chim. Polonorum, 38 (1964), pp. 1625-1633.
Gannett, P.M. et al.; "The Capsaicinoids: Their Separation, Synthesis, and Mutagenictiy"; J. Org. Chem., 53 (1988), pp. 1064-1071.
Motion, K.R. et al.;"Reactions of Diene-conjugated 1,3-Dipolar Intermediates: the Formation of Cyclopropa[c]isoquinolines from Benzonitrile o-Alkenylbenzyl Ylides and their Rearrangements to Benzazepines"; J. Chem. Soc. Perkin Trans., 1 (1992), pp. 1709-1719.
Xu, B. et al.; "Acyclic Analogues of Adenosine Bisphosphates as P2Y Receptor Antagonists: Phosphate Substitution Leads to Multiple Pathways of Inhibiition of Platelet Aggregation"; J. Med. Chem. 45 (2002), pp. 5694-5709.
G. Trapani, et al., "Propofol Analogues. Synthesis, Relationships between Structure and Affinity at $GABA_A$ Receptor in Rat Brain and Differential Electrophysiological Profile at Recombinant Human $GABA_A$ Receptors," J. Med. Chem. 41 (1998) pp. 1846-1854.
G.G. Ecke, et al., "orth-Alkylation of Aromatic Amines," J. Org. Chem., vol. 22, (1957) pp. 639-642.
C. D. Bedford et al., "Nonquatemary Cholinesterase Reactivators. 3. (3(5)-Substituted 1,2,4-Oxadiaxol-5(3)-aldoximes and 1,2,4-Oxadiazole-5(3)-thiocarbohydroximates as Reactivators of Organphosphonate-Inhibited Eel and Human Acetylcholinesterase in Vitro," J. Med. Chem. 29 (1986), pp. 2174-2183.
D. Dubus, et al., "Synthese De Diheterocycles En Serie Oxadiazole-1,2,4," Annales de Chimie (Paris, France) 10 (1975), pp. 331-336.
B. Hedegaard, et al., "Thiophene Chemistry—XIX," Tetrahedron 27 (1971), pp. 3853-3859.
Fujii et al., "Transition Metal-Catalyzed Intramolecular Cyclization of 1,5- and 1,6-Dienes via Direct Cleavage and Addition of the Carbon-Hydrogen Bond," Bull. Chem.. Soc. Jpn., vol. 71, 1998, pp. 285-298.
Yamagata, K. et al., "Studies on Heterocyclic Enaminonitriles. II. 1) Synthesis and Aromatization of 2-Amino-3-cyano-4,5-dihydrothiophenes," Chemical & Pharmaceutical Bulletin 30 (1982), pp. 4396-4401.
Thiemann, Thies et al.; "One pot Suzuki coupling—Wittig olefination reactions", Journal of Chemical Research Nov. 2004, pp. 723-727.

PYRIDINE DERIVATIVES

FIELD OF THE INVENTION

The present invention relates to S1P1/EDG1 receptor agonists of Formula (I) and their use as active ingredients in the preparation of pharmaceutical compositions. The invention also concerns related aspects including processes for the preparation of the compounds, pharmaceutical compositions containing a compound of the Formula (I), and their use as compounds improving vascular function and as immunomodulating agents, either alone or in combination with other active compounds or therapies.

BACKGROUND OF THE INVENTION

The human immune system is designed to defend the body against foreign microorganisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-infammatory drugs (NSAIDs) can reduce pain and inflammation, however, they exhibit considerable side effects. Alternative treatments include agents that activate or block cytokine signaling.

Orally active compounds with immunomodulating properties, without compromising immune responses and with reduced side effects would significantly improve current treatments of uncontrolled inflammatory disease.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DESCRIPTION OF THE INVENTION

The present invention provides novel compounds of Formula (I) that are agonists for the G protein-coupled receptor S1P1/EDG1 and have a powerful and long-lasting immunosuppressive effect which is achieved by reducing the number of circulating and infiltrating T- and B-lymphocytes, without affecting their maturation, memory, or expansion. The reduction of circulating T-/B-lymphocytes as a result of S1P1/EDG1 agonism, possibly in combination with the observed improvement of endothelial cell layer function associated with S1P1/EDG1 activation, makes such compounds useful to treat uncontrolled inflammatory disease and to improve vascular functionality.

The compounds of the present invention can be utilized alone or in combination with standard drugs inhibiting T-cell activation, to provide a new immunosuppressive therapy with a reduced propensity for infections when compared to standard immunosuppressive therapy. Furthermore, the compounds of the present invention can be used in combination with reduced dosages of traditional immunosuppressant therapies, to provide on the one hand effective immunosuppressive activity, while on the other hand reducing end organ damage associated with higher doses of standard immunosuppressive drugs. The observation of improved endothelial cell layer function associated with S1P1/EDG1 activation provides additional benefits of compounds to improve vascular function.

The nucleotide sequence and the amino acid sequence for the human S1P1/EDG1 receptor are known in the art and are published in e.g.: Hla, T., and Maciag, T. *J. Biol Chem.* 265 (1990), 9308-9313; WO91/15583 published 17 Oct. 1991; WO99/46277 published 16 Sep. 1999. The potency and efficacy of the compounds of Formula (I) are assessed using a GTPγS assay to determine $EC_{50}$ values and by measuring the circulating lymphocytes in the rat after oral administration, respectively (see Examples).

The general terms used hereinbefore and hereinafter preferably have, within this disclosure, the following meanings, unless otherwise indicated:

Where the plural form is used for compounds, salts, pharmaceutical compositions, diseases and the like, this is intended to mean also a single compound, salt, or the like.

Any reference hereinbefore or hereinafter to a compound of Formula (I) is to be understood as referring also to salts (especially pharmaceutically acceptable salts) of a compound of Formula (I), as appropriate and expedient.

Salt-forming groups are groups or radicals having basic or acidic properties. Compounds having at least one basic group or at least one basic radical, for example amino, a secondary amino group not forming a peptide bond or a pyridyl radical, may form acid addition salts, for example with inorganic acids. When several basic groups are present mono- or poly-acid addition salts may be formed.

Compounds having acidic groups, such as a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example TEA or tri-(2-hydroxyethyl)-amine, or heterocyclic bases, for example N-ethyl-piperidine or N,N'-dimethylpiperazine. Mixtures of salts are possible.

Compounds having both acidic and basic groups can form internal salts.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

The expression pharmaceutically acceptable salts encompasses either salts with inorganic acids or organic acids like hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, pamoic acid, stearic acid, glutamic acid, aspartic acid, methanesulfonic acid, ethanedisulfonic acid, p-toluenesulfonic acid, salicylic acid, succinic acid, TFA, and the like that are non toxic to living organisms or in case the compound of Formula (I) is acidic in nature with an inorganic base like an alkali or earth alkali base, e.g. sodium hydroxide, potassium hydroxide, calcium hydroxide and the like. For other examples of pharmaceutically acceptable salts, reference can be made to "Salt selection for basic drugs", *Int. J. Pharm.* (1986), 33, 201-217.

Asymmetric carbon atoms of a compound of Formula (I), if present, may exist in the (R) or (S) configuration. Substituents at a double bond or a ring may be present in cis-(=Z-) or trans (=E-) form. The compounds of Formula (I) may thus be present as mixtures of isomers or preferably as pure isomers. Mixtures can be separated in a manner known per se, e.g. by column chromatography, thin layer chromatography, high performance liquid chromatography, or crystallization.

i) The invention relates to novel pyridine compounds of the Formula (I),

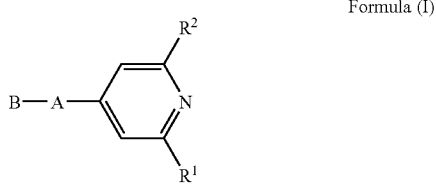

Formula (I)

wherein
A represents *—CO—CH=CH—, *—CO—CH$_2$CH$_2$—,

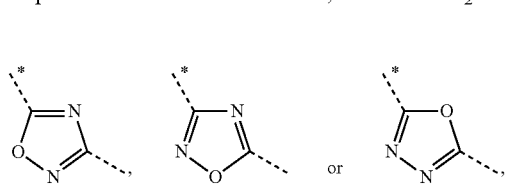

wherein the asterisks indicate the bond that is linked to the group B of Formula (I);
B represents

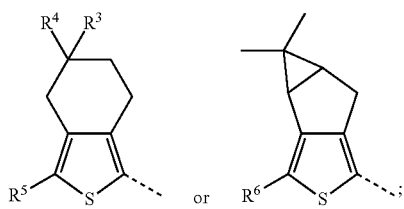

R$^1$ represents hydrogen, methyl, ethyl or chlorine;
R$^2$ represents methyl, ethyl, n-propyl or chlorine;
R$^3$ and R$^4$ represent methyl;
or R$^3$ and R$^4$ represent ethyl;
or R$^3$ and R$^4$ together with the carbon atom to which they are attached form a cyclopropyl, cyclobutyl or cyclopentyl ring;
R$^5$ represents hydrogen, methyl, ethyl, propyl, isopropyl, or trifluoromethyl; and
R$^6$ represents methyl or ethyl;
and salts thereof.

ii) A particular embodiment of the invention relates to pyridine derivatives according to embodiment i), wherein A represents *—CO—CH$_2$—CH$_2$—, wherein the asterisk indicates the bond that is linked to the group B of Formula (I).

iii) Another particular embodiment of the invention relates to pyridine derivatives according to embodiment i), wherein A represents *—CO—CH=CH—, wherein the asterisk indicates the bond that is linked to the group B of Formula (I).

iv) Another particular embodiment of the invention relates to pyridine derivatives according to embodiment i), wherein A represents

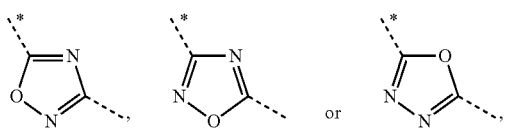

wherein the asterisks indicate the bond that is linked to the group B of Formula (I).

v) A preferred embodiment of the invention relates to pyridine derivatives according to embodiment i), wherein A represents

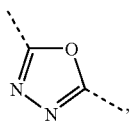

vi) A preferred embodiment of the invention relates to pyridine derivatives according to embodiment i), wherein A represents

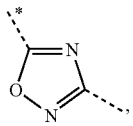

wherein the asterisk indicates the bond that is linked to the group B of Formula (I).

vii) Another preferred embodiment of the invention relates to pyridine derivatives according to any one of the embodiments i) to vi), wherein R$^1$ and R$^2$ represent a methyl group.

viii) Another preferred embodiment of the invention relates to pyridine derivatives according to any one of the embodiments i) to vi), wherein R$^1$ represents a methyl group and R$^2$ represents an ethyl group.

ix) Another particular embodiment of the invention relates to pyridine derivatives according to any one of the embodiments i) to viii), wherein B represents

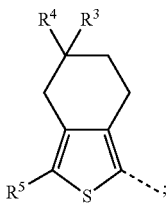

and wherein $R^3$, $R^4$ and $R^5$ are as defined for Formula (I) in embodiment i).

x) Another preferred embodiment of the invention relates to pyridine derivatives according to any one of the embodiments i) to viii), wherein B represents

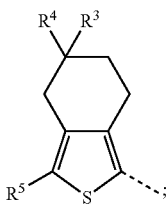

and wherein $R^3$ and $R^4$ represent methyl and $R^5$ represents methyl or ethyl.

xi) Another particular embodiment of the invention relates to pyridine derivatives according to any one of the embodiments i) to viii), wherein B represents

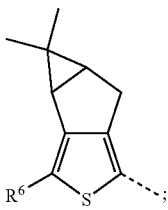

and wherein $R^6$ is as defined for Formula (I) in embodiment i).

xii) Another preferred embodiment of the invention relates to pyridine derivatives according to any one of the embodiments i) to viii), wherein B represents

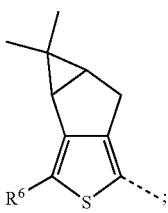

and wherein $R^6$ represents methyl.

xiii) An especially preferred embodiment of the invention relates to pyridine derivatives according to embodiment i), wherein A represents *—CO—CH=CH—, *—CO—CH$_2$CH$_2$—, or

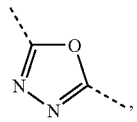

wherein the asterisks indicate the bond that is linked to the group B of Formula (I);
$R^1$ represents methyl, ethyl or chlorine;
$R^2$ represents methyl or ethyl;
$R^3$ and $R^4$ represent methyl;
or $R^3$ and $R^4$ represent ethyl; and
$R^5$ and $R^6$ represent methyl or ethyl.

xiv) Another especially preferred embodiment of the invention relates to pyridine derivatives according to embodiment i), wherein A represents *—CO—CH=CH—, *—CO—CH$_2$CH$_2$—,

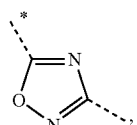

, or

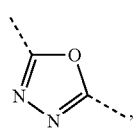

wherein the asterisk indicates the bond that is linked to the group B of Formula (I);
$R^1$ represents methyl, ethyl or chlorine;
$R^2$ represents methyl or ethyl;
$R^3$ and $R^4$ represent methyl;
or $R^3$ and $R^4$ represent ethyl; and
$R^5$ and $R^6$ represent methyl or ethyl.

xv) Specific very preferred pyridine derivatives according to Formula (I) are:
3-(2-ethyl-6-methyl-pyridin-4-yl)-1-((1aS,5aR)-1,1,2-trimethyl-1,1a,5,5a-tetrahydro-3-thia-cyclopropa[a]pentalen-4-yl)-propenone,
1-(3-ethyl-5,5-dimethyl-4,5,6,7-tetrahydro-benzo[c]thiophen-1-yl)-3-(2-ethyl-6-methyl-pyridin-4-yl)-propenone,
3-(2-ethyl-6-methyl-pyridin-4-yl)-1-((1aS,5aR)-1,1,2-trimethyl-1,1a,5,5a-tetrahydro-3-thia-cyclopropa[a]pentalen-4-yl)-propan-1-one,
1-(3-ethyl-5,5-dimethyl-4,5,6,7-tetrahydro-benzo[c]thiophen-1-yl)-3-(2-ethyl-6-methyl-pyridin-4-yl)-propan-1-one,
2-ethyl-6-methyl-4-[5-((1aS,5aR)-1,1,2-trimethyl-1,1a,5,5a-tetrahydro-3-thia-cyclopropa[a]pentalen-4-yl)-[1,3,4]oxadiazol-2-yl]-pyridine,
2,6-diethyl-4-[5-((1aS,5aR)-1,1,2-trimethyl-1,1a,5,5a-tetrahydro-3-thia-cyclopropa[a]pentalen-4-yl)-[1,3,4]oxadiazol-2-yl]-pyridine, 2-chloro-6-methyl-4-[5-((1aS,5aR)-1,1,2-trimethyl-1,1a,5,5a-tetrahydro-3-thia-cyclopropa[a]pentalen-4-yl)-[1,3,4]oxadiazol-2-yl]-pyridine, 2,6-dimethyl-4-[5-((1aS,5aR)-1,1,2-trimethyl-1,1a,5,5a-tetrahydro-3-thia-cyclopropa[a]pentalen-4-yl)-[1,3,4]oxadiazol-2-yl]-pyridine, 2-ethyl-4-[5-(3-ethyl-5,5-dimethyl-4,5,6,7-tetrahydro-benzo[c]thiophen-1-yl)-[1,3,4]oxadiazol-2-yl]-6-methyl-pyridine, 4-[5-(5,5-diethyl-3-methyl-4,5,6,7-tetrahydro-benzo[c]thiophen-1-yl)-[1,3,4]oxadiazol-2-yl]-2-ethyl-6-methyl-pyridine, 4-[5-(3-ethyl-5,5-dimethyl-4,5,6,7-tetrahydro-benzo[c]thiophen-1-yl)-[1,3,4]oxadiazol-2-yl]-2,6-dimethyl-pyridine, 2,6-dimethyl-4-[5-(3,5,5-triethyl-4,5,6,7-tetrahydro-benzo[c]thiophen-1-yl)-[1,3,4]oxadiazol-2-yl]-pyridine, and 2-chloro-4-[5-(3-ethyl-5,5-dimethyl-4,5,6,7-tetrahydro-benzo[c]thiophen-1-yl)-[1,3,4]oxadiazol-2-yl]-6-methyl-pyridine;

and salts of these compounds.

xvi) Further specific very preferred pyridine derivatives according to Formula (i) are:

2-ethyl-6-methyl-4-[5-(1,1,2-trimethyl-1,1a,5,5a-tetrahydro-3-thia-cyclopropa[a]pentalen-4-yl)-[1,2,4]oxadiazol-3-yl]-pyridine, and 2-ethyl-4-[5-(3-ethyl-5,5-dimethyl-4,5,6,7-tetrahydro-benzo[c]thiophen-1-yl)-[1,2,4]oxadiazol-3-yl]-6-methyl-pyridine;

and salts of these compounds.

The compounds of Formula (I) and their pharmaceutically acceptable salts can be used as medicaments, e.g. in the form of pharmaceutical compositions for enteral, parental or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, The Science and Practice of Pharmacy, 20th Edition, Philadelphia College of Pharmacy and Science) by bringing the described compounds of Formula (I) or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

The pharmaceutical compositions comprising a compound of Formula (I) are useful for the prevention and/or treatment of diseases or disorders associated with an activated immune system.

Such diseases or disorders are selected from the group consisting of rejection of transplanted organs, tissue or cells; graft-versus-host diseases brought about by transplantation; autoimmune syndromes including rheumatoid arthritis; systemic lupus erythematosus; antiphospholipid syndrome; Hashimoto's thyroiditis; lymphocytic thyroiditis; multiple sclerosis; myasthenia gravis; type I diabetes; uveitis; episcleritis; scleritis; Kawasaki's disease, uveo-retinitis; posterior uveitis; uveitis associated with Behcet's disease; uveo-meningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; psoriatic arthritis; atopic dermatitis; myopathy; myositis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; scleroderma; alopecia areata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchiolitis; bronchitis; endometriosis; orchitis; gastric ulcers; ischemic bowel diseases; inflammatory bowel diseases; necrotizing enterocolitis; intestinal lesions associated with thermal burns; coeliac disease; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; tubulointerstitial nephritis; interstitial cystitis; multiple myositis; Guillain-Barré syndrome; Meniere's disease; polyneuritis; multiple neuritis; myelitis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; autoimmune thrombocytopenia; agranulocytosis; pernicious anemia; megaloblastic anemia; aneryth-roplasia; osteoporosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; myocarditis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; hypophysitis; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; peripheral artery disease; carcinogenesis; solid cancer tumors; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; and "acute-on-chronic" liver failure.

Preferred diseases or disorders to be treated and/or prevented with the compounds of Formula (I) are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveo-retinitis; atopic diseases such as rhinitis, conjunctivitis, dermatitis; asthma; type I diabetes; post-infectious autoimmune diseases including rheumatic fever and post-infectious glomerulonephritis; solid cancers and tumor metastasis.

Particularly preferred diseases or disorders to be treated and/or prevented with the compounds of Formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis.

The present invention also relates to a method for the prevention or treatment of a disease or disorder mentioned herein comprising administering to a subject a pharmaceutically active amount of a compound of Formula (I).

Furthermore, compounds of the Formula (I) are also useful, in combination with one or several immunomodulating agents, for the prevention and/or treatment of the diseases and disorders mentioned herein. According to a preferred embodiment of the invention, said agents are selected from the group consisting of immunosuppressants, corticosteroids, NSAID's, cytotoxic drugs, adhesion molecule inhibitors, cytokines, cytokine inhibitors, cytokine receptor antagonists and recombinant cytokine receptors.

The present invention also relates to the use of a compound of Formula (I) for the preparation of a pharmaceutical composition, optionally for use in combination with one or several immunomodulating agents, for the prevention and/or treatment of the diseases and disorders mentioned herein.

The present invention also relates to pro-drugs of a compound of Formula (I) that convert in vivo to the compound of Formula (I) as such. Any reference to a compound of Formula (I) is therefore to be understood as referring also to the corresponding pro-drugs of the compound of Formula (I), as appropriate and expedient.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the Formula (I) of the present invention can be prepared according to the general sequence of reactions outlined below. Only a few of the synthetic possibilities leading to compounds of Formula (I) are described. Some instances of the generic groups A and B might be incompatible with the assembly illustrated in schemes 1 through 7 and will thus require the use of protecting groups (PG). Appropriate protecting groups are known to a person skilled in the art and include e.g. a benzyl or a trialkylsilyl group to protect an alcohol, a ketal to protect a diol, etc. These protecting groups may be employed according to standard methodology (e.g. T. W. Greene, P. G. M. Wuts, Protective Groups in Organic Synthesis, 3$^{rd}$ Edition, Wiley New York, 1991; P. J. Kocienski, Protecting Groups, Thieme Stuttgart, 1994). For the purposes of this discussion, it will be assumed that such protecting groups are in place if necessary.

In case A represents —CO—CH=CH—, the compounds of Formula (I) may be prepared by reacting a compound of Structure 2 with a compound of Structure 3 in the presence of a base such as KOtBu, NaOMe, NaOEt, NaOH, KOH, NaH-MDS, LDA or LiHMDS as shown in scheme 1 below. Compounds of Formula (I) wherein A represents —CO—CH$_2$—CH$_2$— may be prepared by reacting a compound of Formula (I) wherein A represents —CO—CH=CH— with hydrogen in the presence of a catalyst such as Pd/C, Pt/C, PtO$_2$, etc. in a solvent such as EtOH, MeOH, THF, etc. A compound of Structure 2 may be prepared by treating a compound of Structure 1 with MeLi in a solvent such as Et$_2$O, THF, dioxane, at temperatures between −20 and 50° C.

Scheme 1: Synthesis of compounds of Formula (I), wherein A represents —CO—CH=CH— or —CO—CH$_2$—CH$_2$—

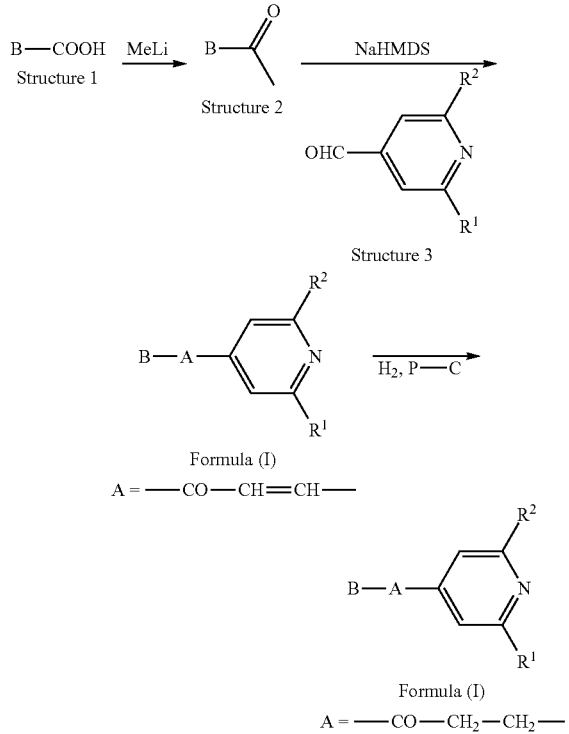

Compounds of Formula (I) which represent a ([1,3,4]oxadiazol-2-yl)-pyridine derivative are prepared by reacting a compound of Structure 4 in a solvent such as THF, dioxane, xylene, toluene, benzene, pyridine, DMF, dichloromethane, etc. at rt, elevated temperatures or using microwave irradiation in the presence or absence of auxiliaries such as acids (e.g. TFA, acetic acid, HCl, etc.), bases (e.g. NaH, NaOAc, Na$_2$CO$_3$, K$_2$CO$_3$, DBU, TEA, etc.), tetraalkylammonium salts, or water removing agents (e.g. Burgess reagent, SOCl$_2$, POCl$_3$, PCl$_5$, P$_4$O$_{10}$, molecular sieves, BF$_3$ etc.) (Lit: e.g. C. T. Brain, J. M. Paul, Y Loong, P. J. Oakley, Tetrahedron Lett. 40 (1999) 3275-3278; F. Bentiss, M. Lagrenée, D. Barbry, Synthetic Comm. 31 (2001) 935-938; V. K. Tandon, R. B. Chhor, Synthetic Comm. 31 (2001) 1727-1732) as shown in scheme 2 below. Compounds of Structure 4 may be prepared by reacting a compound of Structure 1 with a compound of Structure 5 in a solvent such as DMF, THF, DCM etc. in the presence or absence of one or more coupling agents such as TBTU, DCC, EDC/HOBt, HBTU, CDI, PyBOP etc. and in the presence or absence of a base such as TEA, DIPEA, NaH, K$_2$CO$_3$, etc. (Lit: e.g. A. Hamze, J.-F. Hernandez, P. Fulcrand, J. Martinez, J. Org. Chem. 68 (2003) 7316-7321). Alternatively, compounds of Structure 4 may be prepared by reacting a compound of Structure 6 with a compound of Structure 7 using the methods described above.

Scheme 2: Synthesis of compounds of Formula (I) which represent a ([1,3,4]oxadiazol-2-yl)-pyridine derivative

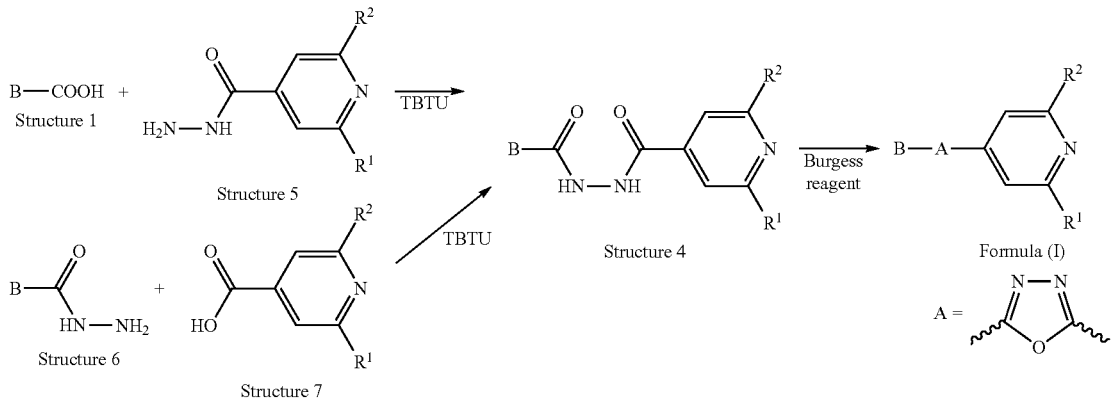

Compounds of Formula (I) which represent a ([1,2,4]oxadiazolyl)-pyridine derivative are prepared as shown in scheme 3 by reacting a compound of Structure 8 or Structure 9, respectively, in a solvent such as xylene, toluene, benzene, pyridine, DMF, DCM etc. at rt, elevated temperatures or using microwave irradiation in the presence or absence of auxiliaries such as acids (e.g. TFA, acetic acid, HCl, etc.), bases (e.g. NaH, NaOAc, $Na_2CO_3$, $K_2CO_3$, TEA, etc.), tetraalkylammonium salts, or water removing agents (e.g. oxalyl chloride, a carboxylic acid anhydride, $POCl_3$, $PCl_5$, $P_4O_{10}$, molecular sieves, etc.) (Lit: e.g. A. R. Gangloff, J. Litvak, E. J. Shelton, D. Sperandio, V. R. Wang, K. D. Rice, *Tetrahedron Lett.* 42 (2001), 1441-1443; T. Suzuki, K. Iwaoka, N. Imanishi, Y. Nagakura, K. Miyta, H. Nakahara, M. Ohta, T. Mase, *Chem. Pharm. Bull.* 47 (1999), 120-122; R. F. Poulain, A. L. Tartar, B. P. Déprez, *Tetrahedron Lett.* 42 (2001), 1495-1498; R. M. Srivastava, F. J. S. Oliveira, D. S. Machado, R. M. Souto-Maior, *Synthetic Commun.* 29 (1999), 1437-1450; E. O. John, J. M. Shreeve, *Inorganic Chemistry* 27 (1988), 3100-3104; B. Kaboudin, K. Navaee, *Heterocycles* 60 (2003), 2287-2292). Compounds of Structure 8 may be prepared by reacting a compound of Structure 1 with a compound of Structure 10 using coupling agents such as TBTU as described before. Compounds of Structure 9 may be prepared by reacting a compound of Structure 11 with a compound of Structure 7 using coupling agents such as TBTU as described above.

Scheme 3: Synthesis of compounds of Formula (I) which represent a ([1,2,4]oxadiazolyl)-pyridine derivative

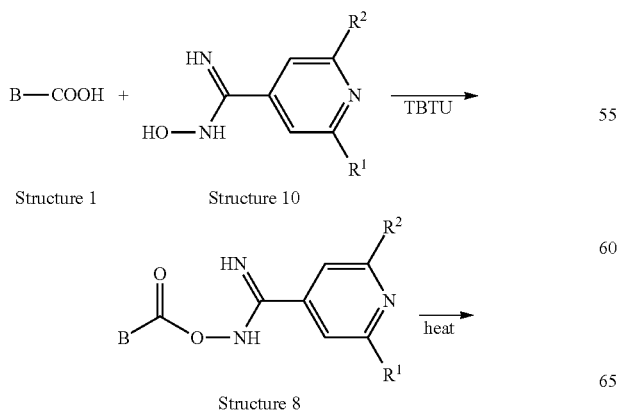

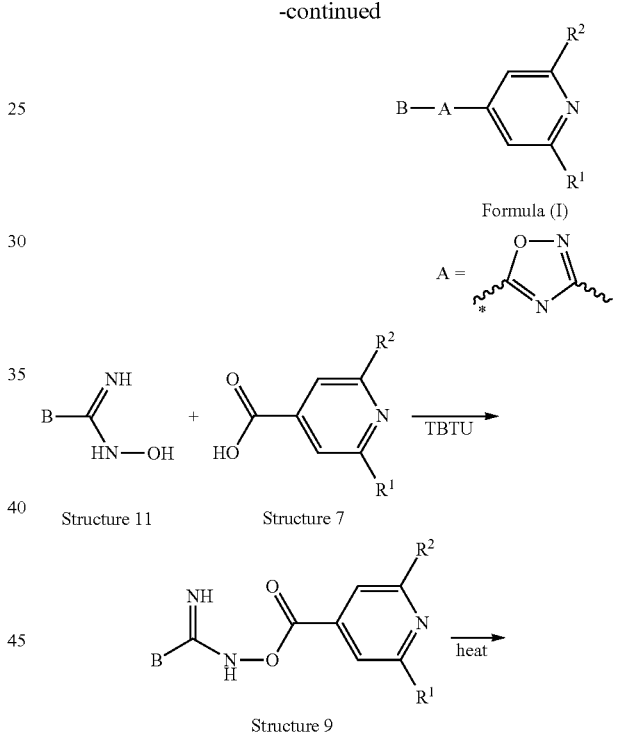

Thiophene intermediates used in schemes 1-3 above are synthesized as shown in scheme 4 below. Compounds of Structure 6 are prepared from thiophene carboxylic acids of Structure 1 by treatment with an acid activating agent such as EDC/HOBt, TBTU, $SOCl_2$ or the like and hydrazine. It is assumed that hydrazine can be protected in form of hydrazinecarboxylic acid tert.-butyl ester or hydrazinecarboxylic acid benzyl ester, the protecting group being removed by methods well-known in the art in a second step. Compounds of Structure 11 may be prepared by reacting cyanothiophenes of Structure 12 with hydroxylamine or one of its salts in a solvent such as MeOH, EtOH, pyridine, etc. in the presence or absence of a base such as $Na_2CO_3$, $K_2CO_3$, TEA, etc. (Lit: e.g. T. Suzuki, K. Iwaoka, N. Imanishi, Y. Nagakura, K. Miyta, H. Nakahara, M. Ohta, T. Mase, *Chem. Pharm. Bull.* 47 (1999), 120-122; J. Cui, D. Crich, D. Wink, M. Lam, A. L. Rheingold, D. A. Case, W. T. Fu, Y. Zhou, M. Rao, A. J. Olson, M. E. Johnson, *Bioorg. Med. Chem.* 11 (2003), 3379-3392; R. Miller, F. Lang, Z. J. Song, D. Zewge, WO 2004/035538 (Merck & Co., Inc., USA); B. Kaboudin, K. Navaee, *Heterocycles* 60 (2003), 2287-2292). Cyanothiophenes of Structure 12 can be prepared in a three-step sequence from thiophene carboxylic acids of Structure 1. In the first step thiophene carbocylic acid acid amides may be obtained by treatment of thiophene carboxylic acids of Structure 1 with an acid activating agent such as EDC/HOBt, TBTU, $SOCl_2$ or the like and followed by treatment with ammonia. Cyanothiophenes of Structure 12 can be prepared from thiophene carbocylic acid amides by dehydration using agents such as TFA anhydride and pyridine in a solvent such as DCM.

Scheme 4: Synthesis of thiophene intermediates

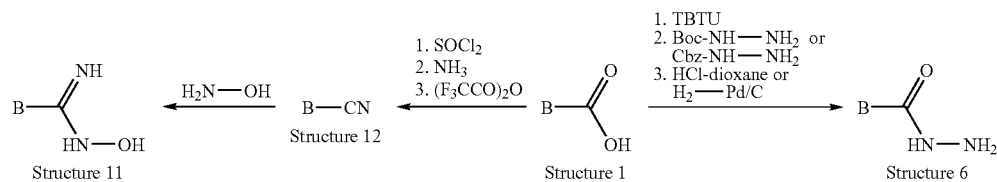

Scheme 5: Synthesis of compounds of Structure 1

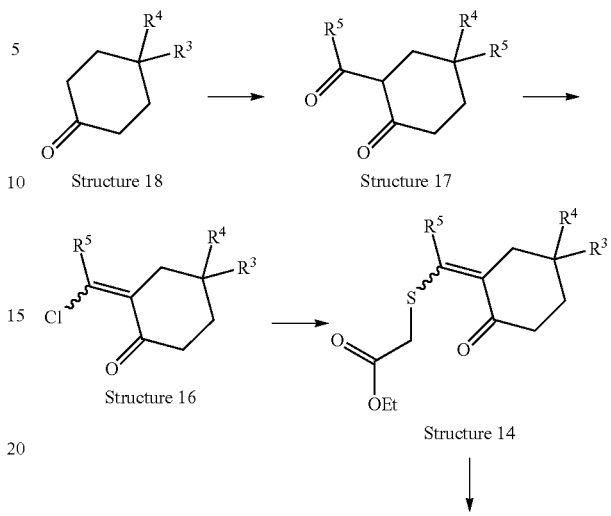

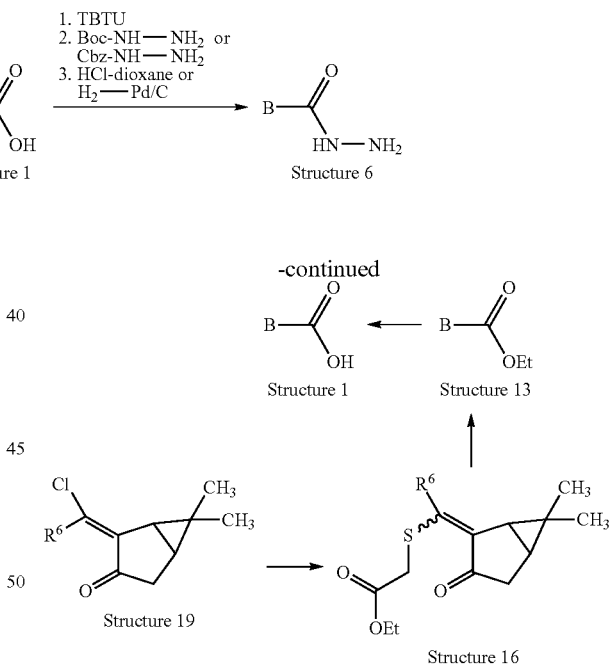

Thiophene carboxylic acids of Structure 1 are synthesized as shown in scheme 5 below. The compound of Structure 1 may be prepared by reacting a compound of Structure 13 with an aqueous base such as aq. NaOH, aq. LiOH, aq. KOH, etc. or an acid such as aq. HCl, TFA, etc. in a solvent such as water, EtOH, MeOH, THF, etc. or mixtures thereof.

The compounds of Structure 13 are prepared by treating a compound of Structure 14 or a compound of Structure 15 with a non-aqueous base such as NaOMe, NaOEt, KOtBu, DBU, etc. in a solvent such as MeOH, EtOH, THF, DMF, etc. or mixtures thereof at rt or preferably at elevated temperatures. The compounds of Structure 14 are prepared by treating a compound of Structure 16 with a 2-mercaptoacetic acid ester in the presence of a base such a NaH, NaOEt, NaOMe, KOtBu, etc. in THF, dioxane, DMF, EtOH, MeOH, etc. or mixtures thereof. Analogously, the compounds of Structure 15 are prepared by treating a compound of Structure 19 with a 2-mercaptoacetic acid ester as described before. In addition, the compounds of Structure 1 may also be prepared in a one-pot three step procedure starting from a compound of Structure 16 or a compound of structure 19 following the above reaction sequence. Nitriles of Structure 12 may be prepared by analogous methods from a compound of Structure 16 or a compound of Structure 19 by replacing the 2-mercaptoacetic acid ester with 2-mercaptoacetonitrile prepared in situ from S-acetylmercaptoacetonitrile (Lit: e.g. W.-Y. Ren, K. V. B. Rao, R. S. Klein, *J. Heterocyclic Chem.* 23 (1986), 1757-1763).

The compounds of Structure 16 are prepared by reacting a compound of Structure 17 with a chlorinating agent such as oxalylchloride in a solvent such as DCM, $CHCl_3$, THF, etc. (Lit. e.g. R. E. Mewshaw, Richard E. *Tetrahedron Lett.* 30 (1989), 3753-3756; F. A. Lakhvich, T. S. Khlebnikova, A. A. Akhrem, *Zhurnal Organicheskoi Khimii* 25 (1989), 2541-2549). The compounds of Structure 17 may be prepared by acylating a compound of Structure 18 with an appropriate acylating agent such as ethyl or methyl formate, methyl or ethyl acetate, methyl or ethyl propionate, chloroformate, acetyl chloride, etc. in the presence of a base such as KOtBu, NaOMe, NaH, LDA, etc. in a solvent such as THF, toluene, EtOH etc. at temperatures between 0 and 60° C. (Lit. e.g. Ch. Kashima, S. Shibata, H. Yokoyama, T. Nishio, *Journal of Heterocyclic Chemistry* 40 (2003), 773-782; I. Yavari, Issa, M. Bayat, *Tetrahedron* 59 (2003), 2001-2005; J. P. Konopelski, J. Lin, P. J. Wenzel, H. Deng, G. I. Elliott, B. S. Gerstenberger, *Organic Letters* 4 (2002) 4121-4124; C. Wiles, P. Watts, S. J. Haswell, E. Pombo-Villar, *Tetrahedron Letters* 43 (2002), 2945-2948; R. Faure, A. Frideling, J.-P. Galy, I. Alkorta, J. Elguero, *Heterocycles* 57 (2002) 307-316; via imine: M. Hammadi, D. Villemin, *Synthetic Communications* 26 (1996) 2901-2904). The compounds of Structure 18 are either commercially available or are prepared according to procedures known to a person skilled in the art (Lit. e.g. M. E. Flaugh, T. A. Crowell, D. S. Farlow, *Journal of Organic Chemistry* 45 (1980) 5399-5400; A. M. Badger, M. J. Dimartino, C. K. Mirabelli, E. N. Cheeseman, J. W. Dorman, D. H. Picker, D. A. Schwartz, Eur. Pat. Appl. EP 310321 A2 (1989); N. R. Natale, R. O. Hutchins, *Organic Preparations and Procedures International* 9 (1977), 103-108; L. M. Rice, B. S. Sheth, J. W. Wheeler, *Journal of Heterocyclic Chemistry* 10 (1973) 731-735).

The compounds of Structure 19 may be prepared starting from (+)-3-carene following the procedures given in the literature (W. Cocker, D. H. Grayson, *Tetrahedron Lett.* 51 (1969), 4451-4452; S. Lochynski, B. Jarosz, M. Walkowicz, K. Piatkowski, *J. Prakt. Chem.* (Leipzig) 330 (1988), 284-288; M. Walkowicz, H. Kuczynsky, C. Walkowicz, *Roczniki Chemii Ann. Soc. Chim. Polonorum* 41 (1967), 927-937; H. Kuczynski, M. Walkowicz, C. Walkowicz, K. Nowak, I. Z. Siemion, *Roczniki Chemii Ann. Soc. Chim. Polonorum,* 38 (1964), 1625-1633; A. V. Pol, V. G. Naik, H. R. Sonawane, *Ind. J. Chem. Sect. B,* 19 (1980) 603-604; S. A. Popov, A. Yu. Denisov, Yu. V. Gatilov, I. Yu. Bagryanskaya and A. V. Tkachev, *Tetrahedron Asymmetry* 5 (1994), 479-489; S. A. Popov, A. V. Tkachev, *Synthetic Commun.* 31 (2001), 233-243).

The compounds of Structure 1 may be prepared by starting from the pure (1S,5R)-stereoisomer of Structure 19 ((1S,5R)-isomer of 2-[1-chloro-ethylidene]-6,6-dimethyl-bicyclo[3.1.0]hexan-3-one) which may be prepared starting from commercially available (+)-3-carene according to the procedures given in the literature (e.g. S. A. Popov, A. Yu. Denisov, Yu. V. Gatilov, I. Yu. Bagryanskaya and A. V. Tkachev, *Tetrahedron Asymmetry* 5 (1994), 479-489; S. A. Popov, A. V. Tkachev, *Synthetic Commun.* 31 (2001), 233-243).

Scheme 6: Sythesis of compounds of Structure 1, wherein $R^6$ represents a methyl, ethyl, propyl, or an isopropyl group

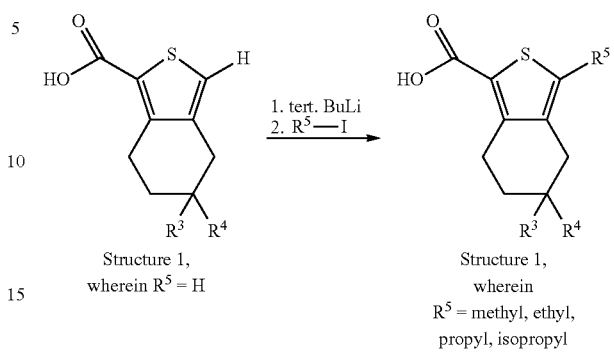

Structure 1, wherein $R^5$ = H

Structure 1, wherein $R^5$ = methyl, ethyl, propyl, isopropyl

The compounds of Structure 1 wherein $R^5$ represents a methyl, ethyl, propyl, or an isopropyl group may also be prepared according to scheme 6 from a compound of Structure 1, wherein $R^5$ represents hydrogen by reacting the latter compound with an excess of a strong base such as n-BuLi, tert.-BuLi, LDA in a solvent such as THF, $Et_2O$, etc. followed by the appropriate alkylating agent (e.g. methyl-, ethyl-, propyl iodide, Lit. e.g. W.-D. Liu, C.-C. Chi, I.-F. Pai, A.-T. Wu, W.-S. Chung, *Journal of Organic Chemistry,* 67 (2002) 9267-9275; D. W. Knight, A. P. Nott, Tetrahedron Letters 21 (1980) 5051-5054; R. Raap, *Canadian Journal of Chemistry* 49 (1971) 2155-2157).

Pyridine intermediates used in schemes 1-3 above are synthesized as shown in scheme 7 below. Isonicotinic acids of Structure 7 are commercially available or are prepared by methods well-known in the art. Acids of Structure 7 can be reduced to pyridine-4-carbaldehydes of Structure 3 by methods well-known in the art such as reacting the acid with reducing agents such as DIBAlH at low temperature in aprotic solvents such as DCM or THF. Alternatively, pyridine-4-carbaldehydes of Structure 3 can be obtained in a two-step sequence by reduction of acids of Structure 7 to 4-hydroxymethyl-pyridines by well-known reagents such as $BH_3$ in THF or $LiAlH_4$ in aprotic solvents such as DCM or THF. 4-Hydroxymethyl-pyridines can be oxidized to pyridine-4-carbaldehydes of Structure 3 by methods well-known in the art such as treatment with $MnO_2$ in solvents such as DCM or $CHCl_3$, Swern oxidation or Dess-Martin oxidation.

Scheme 7: Synthesis of pyridine intermediates

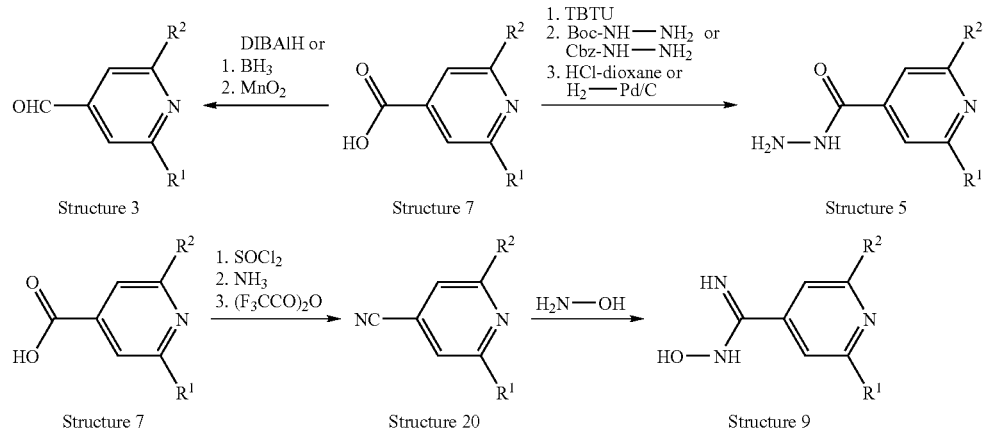

Isonicotinic acid hydrazides of Structure 5 are prepared from isonicotinic acids of Structure 3 by treatment with hydrazine by analogous methods as described in scheme 4 before. It is assumed that hydrazine can be protected in form of hydrazinecarboxylic acid tert.-butyl ester or hydrazinecarboxylic acid benzyl ester, the protecting group being removed by methods well-known in the art in a second step. Hydroxyamidines of Structure 9 may be prepared by reacting isonicotinonitriles of Structure 20 with hydroxylamine or one of its salts by analogous methods as described in scheme 4 before. Isonicotinonitriles of Structure 20 are commercially available or well-known in the art. They can be prepared by methods well-known in the art such as dehydration of isonicotinic acid amides using agents such as TFA anhydride and pyridine in a solvent such as DCM. Isonicotinic acid amides may be obtained by treatment of isonicotinic acids of Structure 7 with an acid activating agent such as EDC/HOBt, TBTU, SOCl$_2$ or the like, followed by treatment with ammonia.

EXAMPLES

The following examples illustrate the invention but do not at all limit the scope thereof.

All temperatures are stated in ° C. Compounds are characterized by $^1$H-NMR (300 MHz) or $^{13}$C-NMR (75 MHz) (Varian Oxford; chemical shifts are given in ppm relative to the solvent used; multiplicities: s=singlet, d=doublet, t=triplet; p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 μm, 120 Å, gradient: 5-95% acetonitrile in water, 1 min, with 0.04% TFA, flow: 4.5 mL/min), $t_R$ is given in min; by TLC (TLC-plates from Merck, Silica gel 60 F$_{254}$); or by melting point. Compounds are purified by preparative HPLC (column: X-terra RP18, 50×19 mm, 5 μm, gradient: 10-95% acetonitrile in water containing 0.5% of formic acid) or by MPLC (Labomatic MD-80-100 pump, Linear UVIS-201 detector, column: 350×18 mm, Labogel-RP-18-5s-100, gradient: 10% methanol in water to 100% methanol).

Abbreviations (as used herein):
abs. absolute
aq. aqueous
atm atmospheric
Bp boiling point
BSA bovine serum albumin
BuLi Butyllithium
Burgess reagent (Methoxycarbonylsulfamoyl)triethylammonium hydroxide
CC column chromatography
CDI 1,1'-carbonyldiimidazol
CHO chinese hamster ovary
d day(s)
DBU 1,8-diazabicyclo[5.4.0]undec-7-en
DCC dicyclohexyl carbodiimide
DCM dichloromethane
DIBAlH Diisobutylaluminiumhydride
DIPEA diisopropyl-ethylamine
DMF dimethylformamide
DMSO dimethylsulfoxide
EA ethyl acetate
EDC N-(3-dimethylaminopropyl)-N'-ethyl-carbodiimide
eq. equivalent(s)
Et ethyl
Et$_2$O diethyl ether
EtOH ethanol
FC flash chromatography
Fe(acac)$_3$ iron(III)-acetylacetonate
GDP guanosine diphosphate
GTP guanosine triphosphate
h hour(s)
HBTU 2-(1H-benzotriazole-1-yl)-1,2,3,3-tetramethyluronium hexafluorophosphate
HEPES N-(2-hydroxyethyl)-piperazine-N'-2-ethanesulfonic acid
HOBt 1-hydroxybenzotriazole
HPLC high performance liquid chromatography
HV high vacuum conditions
KOtBu potassium-tert.-butoxide
LC-MS liquid chromatography-mass spectrometry
LDA lithiumdiisopropylamide
LiHMDS lithiumhexamethyldisilazide
Me methyl
MeLi methyllithium
MeOH methanol
min minute(s)
MPLC medium pressure liquid chromatography
NaHMDS sodiumhexamethyldisilazide
NaOAc sodium acetate
NaOEt sodium ethanolate
NaOMe sodium methanolate
NMP N-methyl-2-pyrrolidone
Pd/C palladium on activated carbon
Pt/C platinum on activated carbon
PyBOP benzotriazol-1-yl-oxy-tris-pyrolidino-phosphonium-hexafluorophosphat
RP reversed phase
rt room temperature
sat. saturated
S1p sphingosine 1-phosphate
TBTU 2-(1H-benzotriazole-1-yl)-1,2,3,3-tetramethyluronium tetrafluoroborate
TEA triethylamine
TFA trifluoroacetic acid
THF tetrahydrofuran
TLC thin layer chromatography
$t_R$ retention time
UV ultra violet Preparation of Intermediates Example A (1aS,5aR)-1,1,2-Trimethyl-1,1a,5,5a-tetrahydro-3-thia-cyclopropa[a]pentalene-4-carboxylic acid a) NaH (7.0 g, 60% dispersion in mineral oil, 175 mmol) is washed with pentane (100 mL) before it is suspended in THF (400 mL). The suspension is cooled at 0° C. and a solution of ethyl 2-mercaptoacetate (12.62 g, 105 mmol) in THF (50 mL) is added over a period of 20 min. The temperature of the reaction is maintained at 5-10° C. Upon completion of the addition, the cooling is removed and stirring is continued for 30 min. A solution of (1S,5R)-2-(1-chloro-(E)-ethylidene)-6,6-dimethyl-bicyclo[3.1.0]hexan-3-one (S. A. Popov, A. Yu. Denisov, Yu. V. Gatilov, I. Yu. Bagryanskaya and A. V. Tkachev, *Tetrahedron Asymmetry* 5 (1994), 479-489; S. A. Popov, A. V. Tkachev; *Synthetic Commun.* 31 (2001), 233-243) (12.93 g, 70 mmol) in THF (50 mL) is added to the suspension and the resulting mixture is stirred for 1.5 h at rt. The mixture is filtered, the filtrate is concentrated to about 100 mL, diluted with 1 M aq. NaOH (100 mL) and extracted twice with DCM (150 mL). The extracts are dried over Na$_2$SO$_4$ and evaporated to furnish a crude E/Z mixture of {1-[(1S,5R)-6,6-dimethyl-3-oxo-bicyclo[3.1.0]hexylidene]-ethylsulfanyl}-acetic acid ethyl ester (18.2 g) as a brown oil. LC-MS: $t_R$=1.00 min, [M+1]+=269.13. $^1$H NMR (CDCl$_3$): δ 4.22 (q, J=7.0 Hz, 2H both isomers), 3.67 (d, J=15.8 Hz, 1H major isomer), 3.63 (d, J=15.8 Hz, 1H minor isomer), 3.58 (d, J=15.8 Hz, 1H major isomer), 3.54 (d, J=15.8 Hz, 1H, minor isomer), 2.67 (dd, J=6.4, 19.4 Hz, 1H minor isomer), 2.60 (dd, J=7.0, 19.4 Hz, 1H major isomer), 2.58 (s, 3H minor isomer), 2.52 (s, 3H major isomer), 2.36-2.32 (m, 1H major isomer), 2.30-2.26 (m, 1H major isomer, 1H minor isomer), 2.18 (d, J=7.0 Hz, 1H minor isomer), 2.00 (d, J=7.0 Hz, 1H major isomer), 1.95 (d, J=7.6 Hz, 1H minor isomer), 1.30 (t, J=7.0 Hz, 3H major isomer), 1.28 (t, J=7.0 Hz, 3H minor isomer), 1.18 (s, 3H major isomer), 1.15 (s, 3H minor isomer), 0.89 (s, 3H minor isomer), 0.85 (s, 3H major isomer).

b) A solution of Na (1.70 g, 74.8 mmol) in abs. EtOH (75 mL) is heated at 60° C. before it is treated with a solution of crude {1-[(1S,5R)-6,6-dimethyl-3-oxo-bicyclo[3.1.0]hex-(2Z)-ylidene]-ethylsulfanyl}-acetic acid ethyl ester (18.2 g, 68.0 mmol) in abs. EtOH (200 mL). The mixture is stirred at 75° C. for 20 min, then cooled to rt, diluted with 0.5 M aq. NaOH (500 mL) and extracted with DCM (450+200 mL). The combined extracts are dried over Na$_2$SO$_4$, filtered and the solvent is removed in vacuo. This yields crude (1aS,5aR)-1, 1,2-trimethyl-1,1a,5,5a-tetrahydro-3-thia-cyclopropa[a]pentalene-4-carboxylic acid ethyl ester (10.5 g) as a yellow oil of 87% puritiy (LC-MS, UV 280 nm). LC-MS: $t_R$=1.11 min, [M+1]$^+$=251.14; $^1$H NMR (CDCl$_3$): δ 4.26 (q, J=7.0 Hz, 2H), 2.95 (dp, J$_d$=18.8 Hz, J$_p$=3.5 Hz, 1H), 2.79 (d, J=19.3, 1H), 2.37 (s, 3H), 1.89-1.84 (m, 2H), 1.34 (t, J=7.0 Hz, 3H), 1.12 (s, 3H), 0.72 (s, 3H).

c) To a solution of crude (1aS,5aR)-1,1,2-trimethyl-1,1a, 5,5a-tetrahydro-3-thia-cyclopropa[a]pentalene-4-carboxylic acid ethyl ester (10.3 g, 41.2 mmol) in EtOH (200 mL) a solution of 2N aq. LiOH (300 mL) is added. The resulting mixture is stirred at 70° C. for 1 h, cooled to rt and diluted with water (250 mL). The aq. solution is extracted three times with DCM (125 mL) before it is acidified to pH 3 by adding citric acid. The acidified solution is extracted twice with DCM (2×250 mL), These second extracts are combined, dried over Na$_2$SO$_4$, filtered and evaporated to give (1aS,5aR)-1,1,2-trimethyl-1,1a,5,5a-tetrahydro-3-thia-cyclopropa[a]pentalene-4-carboxylic acid (7.0 g) as a yellow solid. LC-MS: $t_R$=0.95 min, [M+1]$^+$=223.00. $^1$H NMR (CDCl$_3$): δ 3.04-2.92 (m, 1H), 2.83 (d, J=19.3 Hz, 1H), 2.39 (s, 3H), 1.91-1.87 (m, 2H), 1.13 (s, 3H), 0.73 (s, 3H).

Example B 5,5-Dimethyl-4,5,6,7-tetrahydro-benzo[c]thiophene-1-carboxylic acid a) To a solution of 4,4-dimethyl-cyclohex-2-enone (50 g, 403 mmol) in EA (230 mL), a suspension of Pd/C (2.5 g, 10% Pd) in EA is added. The suspension is stirred at rt for 2 h under 1 bar H$_2$. The catalyst is filtered off and the solvent of the filtrate is carefully evaporated to give 4,4-dimethyl-cyclohexanone (50 g) as a colourless oil which slowly crystallizes; $^1$H NMR (CDCl$_3$): δ 2.34 (t, J=6.4 Hz, 4H), 1.66 (t, J=6.4 Hz, 4H), 1.09 (s, 6H).

b) To an ice-cold solution of KOtBu (24.5 g, 109 mmol, 50% solution in tert.-butanol) in THF (700 mL), ethylformate (120 mL, 123 mmol) is slowly added. The mixture is stirred at rt for 30 min before a solution of 4,4-dimethyl-cyclohexanone (50 g, 396 mmol) in ethylformate (50 mL) and THF (70 mL) is added over a period of 20 min. Upon complete addition, stirring is continued at 15-20° C. for 30 min. The orange suspension is pourred onto 10% aq. citric acid solution (200 mL) and brine (200 mL) and extracted with EA (2×200 mL). The organic extracts are washed with 0.2 N aq. NaOH and brine, dried over Na$_2$SO$_4$ and evaporated to dryness to give 5,5-dimethyl-2-oxo-cyclohexanecarbaldehyde (52 g) as a yellow oil; LC-MS: $t_R$=0.89 min, [M+1+CH$_3$CN]$^+$=196.15.

c) To a solution of 5,5-dimethyl-2-oxo-cyclohexanecarbaldehyde (51 g, 331 mmol) in chloroform (250 mL), oxalyl chloride (40 mL, 465 mmol) is rapidly added. After stirring for 3-4 min ice followed by 2 N aq. NaOH (100 mL) is added. The organic phase is separated and the aq. phase is extracted once more with chloroform. The combined organic extracts are washed with water and dried over Na$_2$SO$_4$. The solvent is removed in vacuo to give 2-chloromethylene-4,4-dimethyl-cyclohexanone (50 g) as a brown oil; LC-MS: $t_R$=0.96 min.

d) To a part (300 mL) of a freshly prepared solution of sodium (21 g, 875 mmol) in EtOH (500 mL), mercaptoacetic acid ethyl ester (50 mL) is added. The resulting solution is added over a period of 10 min to a solution of 2-chloromethylene-4,4-dimethyl-cyclohexanone (50 g, 290 mmol) in THF (170 mL). The mixture becomes warm (50° C.). Upon complete addition, the remaining part of the freshly prepared solution of sodium in EtOH (200 mL) is added to the reaction mixture. The mixture is stirred at rt for 15 min before 1 N aq. LiOH solution (300 mL) is added. The solution is refluxed for 3 h, then stirred at rt for 16 h. The THF and EtOH are removed under reduced pressure and the remaining dark solution is extracted with heptane/EA 3:1 (2×200 mL). The aqueous phase is acidified by adding citric acid (30 g) and 2 N aq. HCl (200 mL) and then extracted three times with EA. The combined organic extracts are washed three times with sat. aq. NaHCO$_3$ solution, dried over Na$_2$SO$_4$ and evaporated. The resulting dark brown oil is dissolved in acetonitrile at 60° C. and crystallised at 5° C. The crystals are collected, washed with acetonitrile and dried to give 5,5-dimethyl-4,5,6,7-tetrahydro-benzo[c]thiophene-1-carboxylic acid (31 g) as a slightly grey powder; LC-MS: $t_R$=0.95 min, [M+1+CH$_3$CN]$^+$=252.18; $^1$H NMR (CDCl$_3$): δ 7.15 (s, 1H), 3.05 (t, J=7.0 Hz, 2H), 2.47 (s, 2H), 1.58 (t, J=7.0 Hz, 2H), 0.97 (s, 6H).

Example C

3-Ethyl-5,5-dimethyl-4,5,6,7-tetrahydro-benzo[c]thiophene-1-carboxylic acid

To a cooled solution (−78° C.) of 5,5-dimethyl-4,5,6,7-tetrahydro-benzo[c]thiophene-1-carboxylic acid (960 mg, 4.57 mmol) in THF (19 mL), tert.-BuLi (8 mL, 1.5 M solution in pentane) is added. The mixture is stirred at −78° C. for 10 min before ethyliodide (3.80 g, 24.37 mmol) is added. The reaction mixture is stirred at −78° C. for 3 h. Water/MeOH 1:1 (8 mL) followed by 10% aq. citric acid solution is added and the mixture is extracted with EA. The combined organic extracts are washed with brine, dried over Na$_2$SO$_4$ and evaporated. The remaining solid is suspended in acetonitrile (6 mL), heated to 60° C., cooled to rt, filtered and dried to give 3-ethyl-5,5-dimethyl-4,5,6,7-tetrahydro-benzo[c]thiophene-1-carboxylic acid (640 mg) as a slightly beige solid; LC-MS: $t_R$=1.01 min, [M+1+CH$_3$CN]=280.10.

Example D 5,5-Diethyl-4,5,6,7-tetrahydro-benzo[c]thiophene-1-carboxylic acid a) A mixture of 2-ethylbutyraldehyde (12.3 mL, 100 mmol), methylvinylketone (5.6 mL, 67.3 mmol) and H$_2$SO$_4$ (0.07 mL) is stirred at 40° C. overnight. Another portion of methylvinylketone (5.6 mL, 67.3 mmol) and $H_2SO_4$ is added and stirring is continued at 40° C. for 2 d. The yellow solution is diluted with chloroform and the solvent is removed again under reduced pressure. The crude product is purified by vacuum distillation to give 4,4-diethyl-cyclohex-2-enone (10.7 g) as a colourless oil; $Bp_{11\ mbar}$=88° C.; $^1$H NMR ($CDCl_3$): δ 6.71 (d, J=10.0 Hz, 1H), 5.92 (d, J=10.5 Hz, 1H), 2.42 (t, J=7.0 Hz, 2H), 1.84 (t, J=7.0 Hz, 2H), 1.57-1.40 (m, 4H), 0.87 (t, J=7.6 Hz, 6H).

b) A solution of 4,4-diethyl-cyclohex-2-enone (10.7 g, 70.5 mmol) in EA (400 mL) is treated with Pd/C (1.0 g, 10% Pd). The suspension is stirred at rt for 24 h under 1 bar of $H_2$. The mixture is filtered, and the filtrate is evaporated to give 4,4-diethyl-cyclohexanone (11.7 g) as a colourless solid; $^1$H NMR ($CD_3OD$): δ 2.32 (t, J=7.0 Hz, 4H), 1.66 (t, J=7.0 Hz, 4H), 1.48 (q, J=7.6 Hz, 4H), 0.88 (t, J=7.6 Hz, 6H).

c) To a suspension of KOtBu (9.19 g, 81.9 mmol) in THF (250 mL), ethylformate (24.8 mL, 260 mmol) is slowly added. To the slightly turbid mixture a solution of 4,4-diethyl-cyclohexanone (11.5 g, 74.4 mmol) in ethyl formate (14 mL, 150 mmol) is added. The mixture becomes warm and is cooled with an ice-bath. The dark red to brown suspension is stirred at rt for 18 h before 10% aq. citric acid is added. The mixture is extracted with DCM and the organic extract is dried over $Na_2SO_4$ and evaporated. The brown oil is dissolved in chloroform (150 mL) and treated with oxaxylchloride (11.3 g, 89.1 mmol). After gas evolution has stopped, the mixute is stirred for 1 h at rt. The dark solution is washed with 2 N aq. NaOH, dried over $Na_2SO_4$ and evaporated to leave a black oil (11.2 g). A solution of this oil in THF (60 mL) is added to a cold solution (3° C.) of NaOEt (11.4 g, 167 mmol) and mercaptoacetic acid ethyl ester (10.0 g, 83.6 mmol) in EtOH (300 mL). The reaction mixture is stirred at rt for 2 h before another portion of NaOEt (5.69 g, 83.6 mmol) is added. Stirring is continued at rt for 16 h and at 60° C. for 2 h. The mixture is diluted with 2 N aq. HCl and is extracted twice with DCM. The combined organic extracts are dried over $Na_2SO_4$, filtered and the solvent is removed in vacuo to give crude 5,5-diethyl-4,5,6,7-tetrahydro-benzo[c]thiophene-1-carboxylic acid ethyl ester (14.2 g) as a brown oil; LC-MS: $t_R$=1.16 min.

d) A solution of 5,5-diethyl-4,5,6,7-tetrahydro-benzo[c]thiophene-1-carboxylic acid ethyl ester (14.2 g, 53.38 mmol) in EtOH (250 mL) and 2 N aq. LiOH (250 mL) is stirred at 65° C. for 18 h. The mixture is diluted with 1 N aq. NaOH and extracted with $Et_2O$. The aq. phase is acidified to pH 2 with 2 N aq. HCl and extracted with DCM. The combined DCM extracts are dried over $Na_2SO_4$, filtered, and the solvent is removed in vacuo. The crude product (11.3 g) is purified by MPLC on RP-$C_{18}$ silica gel to give 5,5-diethyl-4,5,6,7-tetrahydro-benzo[c]thiophene-1-carboxylic acid (2.93 g) as a brown oil; LC-MS: $t_R$=1.01 min, [M+1+$CH_3CN$]=280.19; $^1$H NMR ($CDCl_3$): δ 7.12 (s, 1H), 2.99 (t, J=7.0 Hz, 2H), 2.46 (s, 2H), 1.59 (t, J=7.0 Hz, 2H), 1.40-1.20 (m, 4H), 0.84-0.74 (m, 6H).

Example E 5,5-Diethyl-3-methyl-4,5,6,7-tetrahydro-benzo[c]thiophene-1-carboxylic acid 5,5-Diethyl-3-methyl-4,5,6,7-tetrahydro-benzo[c]thiophene-1-carboxylic acid is prepared from 5,5-diethyl-4,5,6,7-tetrahydro-benzo[c]thiophene-1-carboxylic acid by treatment with tert.-BuLi followed by methyliodide in analogy to Example C; LC-MS: $t_R$=1.03 min, [M+1+$CH_3CN$]=294.27.

Example F 3,5,5-Triethyl-4,5,6,7-tetrahydro-benzo[c]thiophene-1-carboxylic acid 3,5,5-Triethyl-4,5,6,7-tetrahydro-benzo[c]thiophene-1-carboxylic acid is prepared from 5,5-diethyl-4,5,6,7-tetrahydro-benzo[c]thiophene-1-carboxylic acid by treatment with tert.-BuLi followed by ethyliodide in analogy to Example C; LC-MS: $t_R$=1.07 min, [M+1+$CH_3CN$]=308.14.

Example G (1aS,5aR)-1-(1,1,2-Trimethyl-1,1a,5,5a-tetrahydro-3-thia-cyclopropa[a]pentalen-4-yl)-ethanone To a solution of (1aS,5aR)-1,1,2-trimethyl-1,1a,5,5a-tetrahydro-3-thia-cyclopropa[a]pentalene-4-carboxylic acid (220 mg, 1.00 mmol) in $Et_2O$ (10 mL) is added a solution of MeLi (1.6 M, 1.4 mL, 2.10 mmol) in $Et_2O$ at such a pace that the reaction mixture is refluxing gently. Upon completion of the addition, stirring is continued at rt for 30 min. The reaction is quenched by adding sat. aq. $NH_4Cl$ (3 mL). The organic layer is separated, dried over $Na_2SO_4$ and the solvent is evaporated to give (1aS,5aR)-1-(1,1,2-trimethyl-1,1a,5,5a-tetrahydro-3-thia-cyclopropa[a]pentalen-4-yl)-ethanone (165 mg) as a pale yellow oil; LC-MS: $t_R$=1.03 min, [M+1]$^+$=221.20; $^1$H NMR ($CDCl_3$): δ 3.00 (ddd, J=1.8, 4.7, 18.8 Hz, 1H), 2.80 (d, J=18.8 Hz, 1H), 2.38 (s, 6H), 1.93-1.90 (m, 2H), 1.14 (s, 3H), 0.74 (s, 3H).

Example H 1-(3-Ethyl-5,5-dimethyl-4,5,6,7-tetrahydro-benzo[c]thiophen-1-yl)-ethanone To a solution of 3-ethyl-5,5-dimethyl-4,5,6,7-tetrahydro-benzo[c]thiophene-1-carboxylic acid (2.10 g, 8.81 mmol) in $Et_2O$ (100 mL), a solution of methyllithium (11 mL, 1.6 M solution in $Et_2O$) is added at rt. The pale yellow solution is stirred at rt for 15 min before another portion of methyl-lithium (2 mL) is added. Stirring is continued for 15 min, a further portion of methyllithium (1 mL) is added, and the mixture is again stirred for 15 min at rt. The reaction is quenched with water. The organic layer is separated, washed once more with water, dried over $MgSO_4$ and evaporated. The crude product is purified by CC on silica gel eluting with heptane:EA 7:3 to give 1-(3-ethyl-5,5-dimethyl-4,5,6,7-tetrahydro-benzo[c]thiophen-1-yl)-ethanone (1.65 g) as a pale yellow solid; LC-MS: $t_R$=1.00 min, [M+1]=237.15; $^1$H NMR ($CDCl_3$): δ 3.03 (t, J=7.0 Hz, 2H), 2.73 (q, J=7.6 Hz, 2H), 2.47 (s, 3H), 2.31 (s, 2H), 1.55 (t, J=7.0 Hz, 2H), 1.28 (t, J=7.6 Hz, 3H), 0.97 (s, 6H).

Example I 1,1,2-Trimethyl-1,1a,5,5a-tetrahydro-3-thia-cyclopropa[a]pentalene-4-carboxylic acid hydrazide a) To a solution of (1aS,5aR)-1,1,2-trimethyl-1,1a,5,5a-tetrahydro-3-thia-cyclopropa[a]pentalene-4-carboxylic acid (2.2 g, 9.9 mmol), hydrazinecarboxylic acid benzyl ester (3.38 g, 20.4 mmol) and DIPEA (2 mL) in DCM (50 mL) is added TBTU (3.2 g, 10 mmol). The mixture is stirred at rt for 20 h. The mixture is diluted with Et$_2$O (200 mL) and extracted with 1 M aq. NaOH (3×50 mL) and 1 M aq. HCl (2×50 mL). The organic phase is dried (Na$_2$SO$_4$), filtered and evaporated to give crude N'-(1,1,2-trimethyl-1,1a,5,5a-tetrahydro-3-thia-cyclopropa[a]pentalene-4-carbonyl)-hydrazinecarboxylic acid benzyl ester; LC-MS: $t_R$=1.01 min, [M+1]$^+$=371.25.

b) The residue is dissolved in MeOH (100 mL) and 10% Pd—C (600 mg) is added. The mixture is hydrogenated at atm pressure (H$_2$-ballon) for 6 d. The mixture is filtered and evaporated, the residue taken up in 1M aq. HCl (100 mL) and extracted with Et$_2$O (2×30 mL). The aq. phase is basified (33% aq. KOH) and extracted with EA (5×50 mL). The organic extracts are dried (Na$_2$SO$_4$), filtered, evaporated and dried to give 1,1,2-trimethyl-1,1a,5,5a-tetrahydro-3-thia-cyclopropa[a]pentalene-4-carboxylic acid hydrazide as a light yellow-brown foam; LC-MS: $t_R$=0.76 min, [M+1]$^+$=237.20; $^1$H NMR (CD$_3$OD): δ 2.93 (dd, J=18.5, 5.9 Hz, 1H), 2.80 (s, 2H), 2.77 (d, J=18.2 Hz, 1H), 2.33 (s, 3H), 1.86-1.92 (m, 2H), 1.10 (s, 3H), 0.70 (s, 3H).

Example J

2-Ethyl-6-methyl-isonicotinic acid a) N,N-dimethylformamide-di-tert.-butyl-acetal (19 mL, 80 mmol) is added during 40 min to a hot (65° C., flask temperature) suspension of 2-chloro-6-methyl-isonicotinic acid (3.40 g, 19.8 mmol) in dry toluene (100 mL). The clear orange solution is stirred at 80° C. for 48 h, cooled to rt and diluted with toluene (100 mL). The solution is washed with water (2×40 mL), sat. aq. NaHCO$_3$ (3×30 mL) and sat. aq. NaCl (25 mL), dried (Na$_2$SO$_4$), filtered and evaporated. The residue is purified by FC (SiO$_2$, DCM-MeOH) to give 2-chloro-6-methyl-isonicotinic acid tert-butyl ester.

b) A solution of ethylmagnesiumbromide (freshly prepared from ethylbromide (392 mg, 3.6 mmol) and magnesium (83 mg, 3.4 mmol)) in Et$_2$O (10 mL) is added to a cooled (−40° C.) and mechanically stirred solution of 2-chloro-6-methyl-isonicotinic acid tert-butyl ester (0.76 g, 3.34 mmol), Fe(acac)$_3$ (21.2 mg, 0.06 mmol) and NMP (0.6 mL) in THF (60 mL). The mixture is warmed to rt during 0.5 h, diluted with Et$_2$O (150 mL) and quenched with aq. KHSO$_4$ (1 M, 40 mL). The phases are separated and the aq. phase is extracted with Et$_2$O (2×50 mL). The combined organic extracts are dried (MgSO$_4$), filtered and evaporated. The residue is purified by reversed phase MPLC to give 2-ethyl-6-methyl-isonicotinic acid tert-butyl ester; LC-MS: $t_R$=0.67 min, [M+1]$^+$=222.19; $^1$H NMR (CDCl$_3$): δ 7.44 (s, 2H), 2.83 (q, J=7.6 Hz, 2H), 2.58 (s, 3H), 1.59 (s, 9H), 1.30 (t, J=7.6 Hz, 3H).

c) A solution of 2-ethyl-6-methyl-isonicotinic acid tert-butyl ester in DCM (10 mL) is treated with TFA (10 mL) and the mixture stirred at rt for 0.5 h. The mixture is evaporated and the residue dried under HV to give 2-ethyl-6-methyl-isonicotinic acid; LC-MS: $t_R$=0.28 min, [M+1]$^+$=166.25.

Example K 2,6-Diethyl-isonicotinic acid 2,6-Diethyl-isonicotinic acid is synthesized from 2,6-dichloro-isonicotinic acid and ethylmagnesiumbromide (2 eq.) according to Example J; LC-MS: $t_R$=0.42 min, [M+1]$^+$=180.11.

Example L

2-Ethyl-6-methyl-pyridine-4-carbaldehyde a) A suspension of 2-ethyl-6-methyl-isonicotinic acid (2.73 g, 16.5 mmol) in THF (30 mL) is treated with borane in THF (1M, 33.1 mL) at rt for 15 h. The mixture is quenched with sat. aq. Na$_2$CO$_3$ (100 mL) and extracted with CHCl$_3$ (5×50 mL). The organic extracts are dried (Na$_2$SO$_4$), filtered and evaporated (50 mbar, 45° C.) to give crude (2-ethyl-6-methyl-pyridin-4-yl)-methanol (2.18 g); LC-MS: $t_R$=0.80 min, [M+1]$^+$=205.32.

b) A solution of crude (2-ethyl-6-methyl-pyridin-4-yl)-methanol (453.6 mg, 3 mmol) in DCM (30 mL) and MnO$_2$ (2.6 g, 30 mmol) is added. The mixture is stirred at rt for 15 h, filtered and evaporated (130 mbar, 45° C.) to give crude 2-ethyl-6-methyl-pyridine-4-carbaldehyde (0.48 g); $^1$H NMR (CDCl$_3$): δ 10.02 (s, 1H), 7.37 (s, 2H), 2.89 (q, J=7.6 Hz, 2H), 2.64 (s, 3H), 1.33 (t, J=7.6 Hz, 3H).

Example M

2-Ethyl-6-methyl-isonicotinic acid hydrazide a) To a solution of 2-ethyl-6-methyl-isonicotinic acid (0.53 g, 3.2 mmol), hydrazinecarboxylic acid tert.-butyl ester (0.43 g, 3.2 mmol) and DIPEA (0.85 mL) in DMF (10 mL) is added TBTU (1.23 g, 3.8 mmol). The mixture is stirred at rt for 3 h. The mixture is diluted with 1M aq. NaOH (50 mL) and extracted with Et$_2$O-EA (1:1, 3×50 mL). The organic extracts are dried (Na$_2$SO$_4$), filtered and evaporated to give crude N'-(2-ethyl-6-methyl-pyridine-4-carbonyl)-hydrazinecarboxylic acid tert-butyl ester.

b) A solution of crude N'-(2-ethyl-6-methyl-pyridine-4-carbonyl)-hydrazinecarboxylic acid tert-butyl ester in dioxane (10 mL) is treated with 4M HCl in dioxane (4 mL) for 6 h. The mixture is evaporated, the residue taken up in MeOH and the 2-ethyl-6-methyl-isonicotinic acid hydrazide hydrochloride is precipitated from Et$_2$O as white foam; $^1$H NMR (CD$_3$OD): δ 8.16 (s, 1H), 8.14 (s, 1H), 3.15 (q, J=7.6 Hz, 2H), 2.87 (s, 3H), 1.46 (t, J=7.6 Hz, 3H).

Example N

2-Ethyl-N-hydroxy-6-methyl-isonicotinamidine a) To a solution of 2-ethyl-6-methyl-isonicotinic acid hydrochloride (1.85 g, 9.18 mmol, Example J) in DMF (90 mL), DIPEA (6.3 mL, 4.75 g, 36.7 mmol)) is added. The mixture is cooled to 0° C. before PyBOP (5.25 g, 10.1 mmol) is added. Stirring is continued at 0° C. for 15 min, then NH$_3$ (64 mL of a 0.5 M solution in dioxane) is added. Stirring is continued for 2 h at rt before the solvent is evaporated under reduced pressure. The residue is dissolved in DCM (80 mL) and pyridine (4.5 mL, 4.39 g, 55.5 mmol) followed by TFA anhydride (6.32 mL, 9.39 g, 44.7 mmol) is added at 0° C. The mixture is stirred at rt for 2 h, before it is diluted with DCM, washed sat. aq. Na$_2$CO$_3$. The organic phase is dried over MgSO$_4$, filtered and evaporated. The crude product is purified by CC on silica gel eluting with heptane:EA 4:1 to give 2-ethyl-6-methyl-isonicotinonitrile (0.675 g) as a yellow oil; $^1$H NMR (CDCl$_3$): δ 1.33 (t, J=7.5 Hz, 3H), 2.61 (s, 3H), 2.86 (q, J=7.5 Hz, 2H), 7.21 (s, 2H).

b) At 0° C., KOtBu (1.81 g, 16.2 mmol) is carefully added to methanol (25 mL). Hydroxylamine hydrochloride (963 mg, 13.9 mmol) is then added to this solution. The suspension is stirred for 30 min before 2-ethyl-6-methyl-isonicotinonitrile (675 mg, 4.62 mmol) is added. The mixture is refluxed for 1 h, the solvent is evaporated. The residue is dissolved in water, extracted three times with EA. The org. extracts are dried over MgSO$_4$, filtered, evaporated and dried under HV to give 2-ethyl-N-hydroxy-6-methyl-isonicotinamidine (897 mg) as a white powder, LC-MS: $t_R$=0.31 min, $[M+1]^+$= 180.32.

Preparation of Final Products

Example 1

3-(2-Ethyl-6-methyl-pyridin-4-yl)-1-((1aS,5aR)-1,1, 2-trimethyl-1,1a,5,5a-tetra hydro-3-thia-cyclopropa [a]pentalen-4-yl)-propenone A solution of NaHMDS (2M in THF, 1.5 mL) is diluted with THF (25 mL) and cooled at −78° C. A solution of (1aS,5aR)-1-(1,1,2-trimethyl-1,1a,5,5a-tetrahydro-3-thia-cyclopropa[a]pentalen-4-yl)-ethanone (328.3 mg, 1.5 mmol) in THF (2 mL) is slowly added and the mixture is stirred for 0.5 h. A solution of 2-ethyl-6-methyl-pyridine-4-carbaldehyde (444.6 mg, 3 mmol) in THF (1 mL) is slowly added. The mixture is stirred for 1 h at −78° C., then warmed to −30° C. and stirred for 1 h. The mixture is cooled at −78° C. and quenched with 1M aq. NaH$_2$PO$_4$ (10 mL). The mixture is diluted with DCM (150 mL) and water (100 mL) and basified with 1M aq. NaOH. The phases are separated, the organic phase dried (Na$_2$SO$_4$), filtered and evaporated. The residue is purified by MPLC (SiO$_2$, EA-hexane) to give 3-(2-ethyl-6-methyl-pyridin-4-yl)-1-(1aS,5aR)-(1,1,2-trimethyl-1,1a,5, 5a-tetrahydro-3-thia-cyclopropa[a]pentalen-4-yl)-propenone (48 mg) as a colorless oil; LC-MS: $t_R$=0.89 min, $[M+1]^+$=352.36.

Additionally, 3-(2-ethyl-6-methyl-pyridin-4-yl)-3-hydroxy-1-(1aS,5aR)-(1,1,2-trimethyl-1,1a,5,5a-tetrahydro-3-thia-cyclopropa[a]pentalen-4-yl)-propan-1-one (165 mg) is obtained. This material is treated with methanesulfonylchloride (1 eq.) and TEA (2 eq.) in DCM (13 mL) at 0° C. The mixture is diluted with DCM (50 mL) and washed with sat. aq. Na$_2$CO$_3$ (30 mL). The organic phase is dried (Na$_2$SO$_4$), filtered and evaporated. The residue is purified by MPLC (SiO$_2$, hexane-EA gradient) to give 3-(2-ethyl-6-methyl-pyridin-4-yl)-1-((1aS,5aR)-1,1,2-trimethyl-1,1a,5,5a-tetrahydro-3-thia-cyclopropa[a]pentalen-4-yl)-propenone (71 mg); LC-MS: $t_R$=0.89 min, $[M+1]^+$=352.36.

Example 2

1-(3-Ethyl-5,5-dimethyl-4,5,6,7-tetrahydro-benzo[c] thiophen-1-yl)-3-(2-ethyl-6-methyl-pyridin-4-yl)-propenone 1-(3-Ethyl-5,5-dimethyl-4,5,6,7-tetrahydro-benzo[c] thiophen-1-yl)-3-(2-ethyl-6-methyl-pyridin-4-yl)-propenone is prepared from 1-(3-ethyl-5,5-dimethyl-4,5,6,7-tetrahydro-benzo[c]thiophen-1-yl)-ethanone and 2-ethyl-6-methyl-pyridine-4-carbaldehyde in analogy to Example 1; LC-MS: $t_R$=0.95 min, [M+1]=368.33.

Example 3

3-(2-Ethyl-6-methyl-pyridin-4-yl)-1-((1aS,5aR)-1,1, 2-trimethyl-1,1a,5,5a-tetrahydro-3-thia-cyclopropa [a]pentalen-4-yl)-propan-1-one A mixture of 3-(2-ethyl-6-methyl-pyridin-4-yl)-1-(1aS, 5aR)-(1,1,2-trimethyl-1,1a,5,5a-tetrahydro-3-thia-cyclopropa[a]pentalen-4-yl)-propenone (154 mg, 0.44 mmol) and 10% Pd on charcoal (20 mg) in MeOH (30 mL) is hydrogenated at rt at 3 bar. The mixture is evaporated and the residue purified by TLC (SiO$_2$, EA) to give 3-(2-ethyl-6-methyl-pyridin-4-yl)-1-((1aS,5aR)-1,1,2-trimethyl-1,1a,5,5a-tetrahydro-3-thia-cyclopropa[a]pentalen-4-yl)-propan-1-one (16 mg) as colorless oil; LC-MS: $t_R$=0.86 min, [M+1]= 354.32.

Example 4

1-(3-Ethyl-5,5-dimethyl-4,5,6,7-tetrahydro-benzo[c] thiophen-1-yl)-3-(2-ethyl-6-methyl-pyridin-4-yl)-propan-1-one 1-(3-Ethyl-5,5-dimethyl-4,5,6,7-tetrahydro-benzo[c] thiophen-1-yl)-3-(2-ethyl-6-methyl-pyridin-4-yl)-propan-1-one is prepared from 1-(3-ethyl-5,5-dimethyl-4,5,6,7-tetrahydro-benzo[c]thiophen-1-yl)-3-(2-ethyl-6-methyl-pyridin-4-yl)-propenone in analogy to Example 3; LC-MS: $t_R$=0.90 min, [M+1]=370.38; $^1$H NMR (CD$_3$OD): δ 6.97 (s, 2H), 3.12 (t, J=7.3 Hz, 2H), 2.98 (t, J=6.7 Hz, 2H), 2.96 (t, J=7.6 Hz, 2H), 2.74 (q, J=7.3 Hz, 2H), 2.70 (q, J=7.6 Hz, 2H), 2.33 (s, 2H), 2.44 (s, 3H), 1.54 (t, J=6.7 Hz, 2H), 1.25 (t, J=7.6 Hz, 3H), 1.22 (t, J=7.6 Hz, 3H), 0.96 (s, 6H).

Example 5

2-Ethyl-6-methyl-4-[5-((1aS,5aR)-1,1,2-trimethyl-1, 1a,5,5a-tetrahydro-3-thia-cyclopropa[a]pentalen-4-yl)-[1,3,4]oxadiazol-2-yl]-pyridine a) To a mixture of 2-ethyl-6-methyl-isonicotinic acid (87.9 mg, 0.53 mmol), 1,1,2-trimethyl-1,1a,5,5a-tetrahydro-3-thia-cyclopropa[a]pentalene-4-carboxylic acid hydrazide (141.8 mg, 0.6 mmol), HOBt (100 mg, 0.74 mmol) and TEA (0.42 mL) in DCM (5 mL) is added at 0° C. EDC (200 mg, 0.78 mmol). The mixture is stirred for 15 h during which time it warmed from 0° C. to rt. The mixture is quenched with EA (50 mL) and washed with 1M aq. NaOH (2×10 mL). The organic phase is dried (Na$_2$SO$_4$), filtered and evaporated to give crude 2-ethyl-6-methyl-isonicotinic acid N'-(1,1,2-trimethyl-1,1a,5,5a-tetrahydro-3-thia-cyclopropa[a]pentalene-4-carbonyl)-hydrazide (350 mg); LC-MS: $t_R$=0.80 min, [M+ 1]=384.34.

b) A mixture of crude 2-ethyl-6-methyl-isonicotinic acid N'-(1,1,2-trimethyl-1,1a,5,5a-tetrahydro-3-thia-cyclopropa [a]pentalene-4-carbonyl)-hydrazide (350 mg, ca. 0.5 mmol) and Burgess Reagent (385 mg, 1.62 mmol) in THF (5 mL) is heated at 110° C. for 3 min in a microwave oven. The mixture is diluted with EA (10 mL) and extracted with sat. aq. Na$_2$CO$_3$ (2×5 mL). The organic phase is dried (Na$_2$SO$_4$), filtered and evaporated to give crude product (50.9 mg) that is purified by HPLC to give 2-ethyl-6-methyl-4-[5-((1aS,5aR)-1,1,2-trimethyl-1,1a,5,5a-tetrahydro-3-thia-cyclopropa[a] pentalen-4-yl)-[1,3,4]oxadiazol-2-yl]-pyridine (16 mg) as a light yellow powder; LC-MS: $t_R$=0.91 min, [M+1]=366.21.

Example 6

2,6-Diethyl-4-[5-((1aS,5aR)-1,1,2-trimethyl-1,1a,5, 5a-tetrahydro-3-thia-cyclopropa[a]pentalen-4-yl)-[1, 3,4]oxadiazol-2-yl]-pyridine 2,6-Diethyl-4-[5-((1aS,5aR)-1,1,2-trimethyl-1,1a,5,5a-tetrahydro-3-thia-cyclopropa[a]pentalen-4-yl)-[1,3,4]oxadiazol-2-yl]-pyridine is synthesized from 1,1,2-trimethyl-1, 1a,5,5a-tetrahydro-3-thia-cyclopropa[a]pentalene-4-carboxylic acid hydrazide and 2,6-diethyl-isonicotinic acid in analogy to Example 5; LC-MS: $t_R$=0.96 min, [M+1]=380.34.

Example 7

2-Chloro-6-methyl-4-[5-((1aS,5aR)-1,1,2-trimethyl-1,1a,5,5a-tetrahydro-3-thia-cyclopropa[a]pentalen-4-yl)-[1,3,4]oxadiazol-2-yl]-pyridine 2-Chloro-6-methyl-4-[5-((1aS,5aR)-1,1,2-trimethyl-1,1a,5,5a-tetrahydro-3-thia-cyclopropa[a]pentalen-4-yl)-[1,3,4]oxadiazol-2-yl]-pyridine is synthesized from 1,1,2-trimethyl-1,1a,5,5a-tetrahydro-3-thia-cyclopropa[a]pentalene-4-carboxylic acid hydrazide and 2-chloro-6-methyl-isonicotinic acid in analogy to Example 5; LC-MS: $t_R$=1.17 min, [M+1]=374.22.

Example 8

2,6-Dimethyl-4-[5-((1aS,5aR)-1,1,2-trimethyl-1,1a,5,5a-tetrahydro-3-thia-cyclopropa[a]pentalen-4-yl)-[1,3,4]oxadiazol-2-yl]-pyridine To a solution of 2-chloro-6-methyl-4-[5-((1aS,5aR)-1,1,2-trimethyl-1,1a,5,5a-tetrahydro-3-thia-cyclopropa[a]pentalen-4-yl)-[1,3,4]oxadiazol-2-yl]-pyridine (62.9 mg, 0.17 mmol), Fe(acac)$_3$ (6 mg) and NMP (20 mg) in THF (5 mL) is added a solution of methylmagnesiumiodide in THF (3M, 0.51 mmol) and the mixture is stirred at rt for 15 h. The mixture is quenched with water (30 mL) and extracted with Et$_2$O (2×50 mL). The organic extracts are dried (MgSO$_4$), filtered and evaporated. The residue is purified by TLC (SiO$_2$, EA-hexane) to give 2,6-dimethyl-4-[5-((1aS,5aR)-1,1,2-trimethyl-1,1a,5,5a-tetrahydro-3-thia-cyclopropa[a]pentalen-4-yl)-[1,3,4]oxadiazol-2-yl]-pyridine (28 mg); LC-MS: $t_R$=0.88 min, [M+1]=352.54.

Example 9

2-Ethyl-4-[5-(3-ethyl-5,5-dimethyl-4,5,6,7-tetrahydro-benzo[c]thiophen-1-yl)-[1,3,4]oxadiazol-2-yl]-6-methyl-pyridine a) To a solution of 3-ethyl-5,5-dimethyl-4,5,6,7-tetrahydro-benzo[c]thiophene-1-carboxylic acid (114 mg, 0.48 mmol), 2-ethyl-6-methyl-isonicotinic acid hydrazide hydrochloride (120.5 mg, 0.48 mmol) and DIPEA (0.49 mL) in DMF (8 mL) is added TBTU (190 mg, 0.59 mmol). The mixture is stirred at rt for 15 h. The mixture is diluted with Et$_2$O (50 mL) and extracted with 1M aq. NaOH (2×20 mL). The aq. extracts are washed with EA (2×20 mL) and the combined organic phases are dried (MgSO$_4$), filtered and evaporated to give crude 3-ethyl-5,5-dimethyl-4,5,6,7-tetrahydro-benzo[c]thiophene-1-carboxylic acid N'-(2-ethyl-6-methyl-pyridine-4-carbonyl)-hydrazide; LC-MS: $t_R$=0.83 min, [M+1]=400.31.

b) A mixture of crude 3-ethyl-5,5-dimethyl-4,5,6,7-tetrahydro-benzo[c]thiophene-1-carboxylic acid N'-(2-ethyl-6-methyl-pyridine-4-carbonyl)-hydrazide (289 mg, ca. 0.48 mmol) and Burgess Reagent (367 mg, 1.6 mmol) in THF (5 mL) is heated at 110° C. for 3 min in a microwave oven. The mixture is diluted with EA (50 mL) and extracted with 1M aq. NaOH (2×10 mL). The organic phase is dried (MgSO$_4$), filtered and evaporated. The residue is purified by HPLC to give 2-ethyl-4-[5-(3-ethyl-5,5-dimethyl-4,5,6,7-tetrahydro-benzo[c]thiophen-1-yl)-[1,3,4]oxadiazol-2-yl]-6-methyl-pyridine (53 mg); LC-MS: $t_R$=0.96 min, [M+1]=382.26.

Example 10

4-[5-(5,5-Diethyl-3-methyl-4,5,6,7-tetrahydro-benzo[c]thiophen-1-yl)-[1,3,4]oxadiazol-2-yl]-2-ethyl-6-methyl-pyridine 4-[5-(5,5-Diethyl-3-methyl-4,5,6,7-tetrahydro-benzo[c]thiophen-1-yl)-[1,3,4]oxadiazol-2-yl]-2-ethyl-6-methyl-pyridine is synthesized from 5,5-diethyl-3-methyl-4,5,6,7-tetrahydro-benzo[c]thiophene-1-carboxylic acid and 2-ethyl-6-methyl-isonicotinic acid hydrazide hydrochloride in analogy to Example 9; LC-MS: $t_R$=0.98 min, [M+1]=396.39.

Example 11

4-[5-(3-Ethyl-5,5-dimethyl-4,5,6,7-tetrahydro-benzo[c]thiophen-1-yl)-[1,3,4]oxadiazol-2-yl]-2,6-dimethyl-pyridine 4-[5-(3-Ethyl-5,5-dimethyl-4,5,6,7-tetrahydro-benzo[c]thiophen-1-yl)-[1,3,4]oxadiazol-2-yl]-2,6-dimethyl-pyridine is synthesized from 3-ethyl-5,5-dimethyl-4,5,6,7-tetrahydro-benzo[c]thiophene-1-carboxylic acid and 2,6-dimethyl-isonicotinic acid hydrazide hydrochloride in analogy to Example 9; LC-MS: $t_R$=0.93 min, [M+1]=368.44; $^1$H NMR (CD$_3$OD): δ 7.66 (s, 2H), 3.09 (t, J=6.7 Hz, 2H), 2.80 (q, J=7.6 Hz, 2H), 2.60 (s, 6H), 2.39 (s, 2H), 1.67 (t, J=6.7 Hz, 2H), 1.29 (t, J=7.6 Hz, 3H), 1.03 (s, 6H).

Example 12

2,6-Dimethyl-4-[5-(3,5,5-triethyl-4,5,6,7-tetrahydro-benzo[c]thiophen-1-yl)-[1,3,4]oxadiazol-2-yl]-pyridine 2,6-Dimethyl-4-[5-(3,5,5-triethyl-4,5,6,7-tetrahydro-benzo[c]thiophen-1-yl)-[1,3,4]oxadiazol-2-yl]-pyridine is synthesized from 3-ethyl-5,5-dimethyl-4,5,6,7-tetrahydro-benzo[c]thiophene-1-carboxylic acid and 2,6-dimethyl-isonicotinic acid hydrazide hydrochloride in analogy to Example 9; LC-MS: $t_R$=0.99 min, [M+1]=396.28.

Example 13

2-Chloro-4-[5-(3-ethyl-5,5-dimethyl-4,5,6,7-tetrahydro-benzo[c]thiophen-1-yl)-[1,3,4]oxadiazol-2-yl]-6-methyl-pyridine 2-Chloro-4-[5-(3-ethyl-5,5-dimethyl-4,5,6,7-tetrahydro-benzo[c]thiophen-1-yl)-[1,3,4]oxadiazol-2-yl]-6-methyl-pyridine is synthesized from 3,5,5-triethyl-4,5,6,7-tetrahydro-benzo[c]thiophene-1-carboxylic acid and 2-chloro-6-methyl-isonicotinic acid hydrazide in analogy to Example 9; LC-MS: $t_R$=1.22 min, [M+1]=388.25.

Example 14

2-Ethyl-6-methyl-4-[5-(1,1,2-trimethyl-1,1a,5,5a-tetrahydro-3-thia-cyclopropa[a]pentalen-4-yl)-[1,2,4]oxadiazol-3-yl]-pyridine a) To a solution of (1aS,5aR)-1,1,2-trimethyl-1,1a,5,5a-tetrahydro-3-thia-cyclopropa[a]pentalene-4-carboxylic acid (64 mg, 289 μmol) and DIPEA (112 mg, 868 μmol) in DMF (3 mL) is added TBTU (98 mg, 306 µmol) at 0° C. The mixture is stirred for 15 min at 0° C. before 2-ethyl-N-hydroxy-6-methyl-isonicotinamidine (55 mg, 306 µmol) is added. Stirring is continued for 1 h at 0° C. The reaction is quenched with water (2 mL), the mixture is diluted in EA, and then washed with sat. aq. NaHCO$_3$ solution followed by water. The org. extract is dried over MgSO$_4$, filtered, and evaporated. The crude product is purified by prep. TLC with heptane:EA 3:2 to give the corresponding hydroxyamidine ester (62 mg) as a yellow oil; LC-MS: $t_R$=0.86 min, [M+1]= 384.10.

b) The above material (62 mg, 162 µmol) is dissolved in dioxane (2 mL) and the solution is stirred at 90° C. for 48 h. The solvent is evaporated and the crude product is purified on prep. TLC plates with heptane:EA 1:1 to give 2-ethyl-6-methyl-4-[5-(1,1,2-trimethyl-1,1a,5,5a-tetrahydro-3-thia-cyclopropa[a]pentalen-4-yl)-[1,2,4]oxadiazol-3-yl]-pyridine (36 mg) as a colourless oil; LC-MS: $t_R$=0.96 min, [M+1]=366.11; $^1$H NMR (CDCl$_3$): δ 0.78 (s, 3H), 1.17 (s, 3H), 1.36 (t, J=7.8 Hz, 3H), 1.94-2.03 (m, 2H), 2.46 (s, 3H), 2.64 (s, 3H), 2.90 (q, J=7.5 Hz, 2H), 2.97 (d, J=19.1 Hz, 1H), 3.13 (dd, J=19.1, 6.5 Hz, 1H), 7.67 (s, 2H).

Example 15

2-Ethyl-4-[5-(3-ethyl-5,5-dimethyl-4,5,6,7-tetrahydro-benzo[c]thiophen-1-yl)-[1,2,4]oxadiazol-3-yl]-6-methyl-pyridine 2-Ethyl-4-[5-(3-ethyl-5,5-dimethyl-4,5,6,7-tetrahydro-benzo[c]thiophen-1-yl)-[1,2,4]oxadiazol-3-yl]-6-methyl-pyridine is prepared in analogy to Example 14 starting from 5,5-dimethyl-4,5,6,7-tetrahydro-benzo[c]thiophene-1-carboxylic acid and 2-ethyl-N-hydroxy-6-methyl-isonicotinamidine; LC-MS: $t_R$=1.01 min, [M+1]=382.15; $^1$H NMR (CDCl$_3$): δ 1.04 (s, 6H), 1.34 (t, J=7.5 Hz, 3H), 1.38 (t, J=7.5 Hz, 3H), 1.67 (t, J=6.5 Hz, 2H), 2.38 (s, 2H), 2.65 (s, 3H), 2.81 (q, J=7.5 Hz, 2H), 2.91 (q, J=7.5 Hz, 2H), 3.17 (t, J=6.5 Hz, 2H), 7.70 (s, 2H).

Example 16

GTPγS assay to determine EC$_{50}$ values

GTPγS binding assays are performed in 96 well microtiter plates (Nunc, 442587) in a final volume of 200 µl, using membrane preparations of CHO cells expressing recombinant human S1P1 receptor. Assay conditions are 20 mM Hepes (Fluka, 54461), 100 mM NaCl (Fluka, 71378), 5 mM MgCl$_2$ (Fluka, 63064), 0.1% BSA (Calbiochem, 126609), 1 µM GDP (Sigma, G-7127), 2.5% DMSO (Fluka, 41644), 50 µM $^{35}$S-GTPγS (Amersham Biosciences, SJ1320). The pH is 7.4. Test compounds are dissolved and diluted in 100% DMSO and pre-incubated at room temperature for 30 min in 150 µl of the above assay buffer, in the absence of $^{35}$S-GTPγS. After addition of 50 µl of $^{35}$S-GTPγS, the assay is incubated for 1 h at rt. The assay is terminated by transfer of the reaction mixture to a Multiscreen plate (Millipore, MAHFC1H60) using a cell harvester from Packard Biosciences, and the plates are washed with ice-cold 10 mM Na$_2$HPO$_4$/NaH$_2$PO$_4$ (70%/30%), dried, sealed at the bottom and, after addition of 25 µl MicroScint20 (Packard Biosciences, order #6013621), sealed on the top. Membrane-bound $^{35}$S-GTPγS is measured with a TopCount from Packard Biosciences.

EC$_{50}$ is the concentration of agonist inducing 50% of the maximal specific $^{35}$S-GTPγS binding. Specific binding is determined by subtracting non-specific binding from maximal binding. Maximal binding is the amount of cpm bound to the Multiscreen plate in the presence of 10 µM of S1P. Non-specific binding is the amount of binding in the absence of an agonist in the assay. Table 1 shows the EC$_{50}$ value of some compounds of the present invention. The EC$_{50}$ values were determined according to the method described above:

TABLE 1

| Compound of Example | EC$_{50}$ [nM] |
|---|---|
| 1 | 1.3 |
| 4 | 4.6 |
| 8 | 3.4 |
| 14 | 3.7 |

Example 17

Assessment of In vivo Efficacy

The efficacy of the compounds of Formula (I) is assessed by measuring the circulating lymphocytes after oral administration of 3 to 30 mg/kg of a compound of Formula (I) to normotensive male Wistar rats. The animals are housed in climate-controlled conditions with a 12 h-light/dark cycle, and have free access to normal rat chow and drinking water. Blood is collected before and 3, 6 and 24 h after drug administration. Full blood is subjected to hematology using Advia Hematology system (Bayer Diagnostics, Zürich, Switzerland).

All data are presented as mean±SEM. Statistical analyses are performed by analysis of variance (ANOVA) using Statistica (StatSoft) and the Student-Newman-Keuls procedure for multiple comparisons. The null hypothesis is rejected when p<0.05.

As an example, Table 2 shows the effect on lymphocyte counts 6 h after oral administration of 10 mg/kg of a compound of the present invention to normotensive male Wistar rats as compared to a group of animals treated with vehicle only.

TABLE 2

| Compound of Example | Lymphocyte counts |
|---|---|
| 5 | −77% |

The invention claimed is:
1. A compound of the Formula (I),

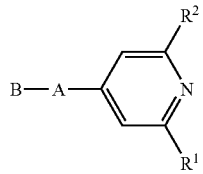

Formula (I)

wherein
A represents

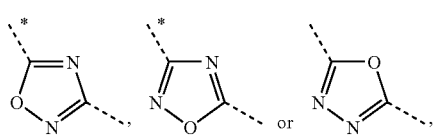

wherein the asterisks indicate the bond that is linked to the group B of Formula (I);

B represents

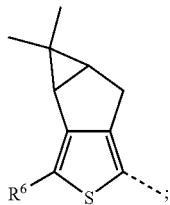

R¹ represents hydrogen, methyl, ethyl or chlorine;
R² represents methyl, ethyl, n-propyl or chlorine; and
R⁶ represents methyl or ethyl;
or a salt thereof.

2. A compound according to claim 1, wherein A represents

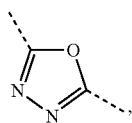

or a salt thereof.

3. A compound according to claim 1, wherein A represents

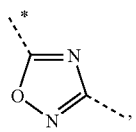

wherein the asterisk indicates the bond that is linked to the group B of Formula (I), or a salt thereof.

4. A compound according to claim 1, wherein R¹ and R² represent a methyl group, or a salt thereof.

5. A compound according to claim 1, wherein R¹ represents a methyl group and R² represents an ethyl group, or a salt thereof.

6. A compound according to claim 1, wherein A represents

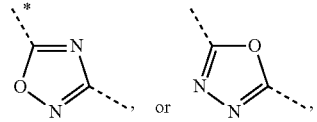

wherein the asterisks indicate the bond that is linked to the group B of Formula (I);
R¹ represents methyl, ethyl or chlorine;
R² represents methyl or ethyl;
and R⁶ represents methyl or ethyl; or a salt thereof.

7. A compound according to claim 1 selected from the group consisting of:
2-ethyl-6-methyl-4-[5-((1aS,5aR)-1,1,2-trimethyl-1,1a,5,5a-tetrahydro-3-thia-cyclopropa[a]pentalen-4-yl)-[1,3,4]oxadiazol-2-yl]-pyridine,
2,6-diethyl-4-[5-((1aS,5aR)-1,1,2-trimethyl-1,1a,5,5a-tetrahydro-3-thia-cyclopropa[a]pentalen-4-yl)-[1,3,4]oxadiazol-2-yl]-pyridine,
2-chloro-6-methyl-4-[5-((1aS,5aR)-1,1,2-trimethyl-1,1a,5,5a-tetrahydro-3-thia-cyclopropa[a]pentalen-4-yl)-[1,3,4]oxadiazol-2-yl]-pyridine, and
2,6-dimethyl-4-[5-((1aS,5aR)-1,1,2-trimethyl-1,1a,5,5a-tetrahydro-3-thia-cyclopropa[a]pentalen-4-yl)-[1,3,4]oxadiazol-2-yl]-pyridine, or a salts thereof.

8. A compound according to claim 1 selected from the group consisting of:
2-ethyl-6-methyl-4-[5-(1,1,2-trimethyl-1,1a,5,5a-tetrahydro-3-thia-cyclopropa[a]pentalen-4-yl)-[1,2,4]oxadiazol-3-yl]-pyridine,
or a salts thereof.

9. A pharmaceutical composition comprising a compound according to claim 1, or a pharmaceutically acceptable salt thereof, and a pharmaceutically acceptable carrier.

* * * * *